US009560995B2

(12) United States Patent
Addison et al.

(10) Patent No.: US 9,560,995 B2
(45) Date of Patent: Feb. 7, 2017

(54) METHODS AND SYSTEMS FOR DETERMINING A PROBE-OFF CONDITION IN A MEDICAL DEVICE

(71) Applicant: Covidien LP, Mansfield, MA (US)

(72) Inventors: Paul Stanley Addison, Edinburgh (GB); James Nicholas Watson, Dunfermline (GB)

(73) Assignee: Covidien LP, Mansfield, MA (US)

( * ) Notice: Subject to any disclaimer, the term of this patent is extended or adjusted under 35 U.S.C. 154(b) by 852 days.

(21) Appl. No.: 13/776,686

(22) Filed: Feb. 25, 2013

(65) Prior Publication Data
US 2014/0243633 A1 Aug. 28, 2014

(51) Int. Cl.
A61B 5/1455 (2006.01)
A61B 5/00 (2006.01)

(52) U.S. Cl.
CPC ......... A61B 5/14552 (2013.01); A61B 5/6844 (2013.01); A61B 5/7221 (2013.01)

(58) Field of Classification Search
CPC .................................................. A61B 5/1455
See application file for complete search history.

(56) References Cited

U.S. PATENT DOCUMENTS

| | | | |
|---|---|---|---|
| 4,621,643 A | 11/1986 | New, Jr. et al. | |
| 5,503,148 A | 4/1996 | Pologe et al. | |
| 5,846,190 A | 12/1998 | Woehrle | |
| 5,924,985 A | 7/1999 | Jones | |
| 5,934,277 A | 8/1999 | Mortz | |
| 6,360,114 B1 | 3/2002 | Diab et al. | |
| 6,385,471 B1 | 5/2002 | Mortz | |
| 6,398,727 B1 | 6/2002 | Bui et al. | |
| 6,510,329 B2 | 1/2003 | Heckel | |
| 6,526,300 B1 | 2/2003 | Kiani et al. | |
| 6,560,470 B1 | 5/2003 | Pologe | |
| 6,600,940 B1 | 7/2003 | Fein et al. | |
| 6,654,624 B2 | 11/2003 | Diab et al. | |
| 6,675,031 B1 | 1/2004 | Porges et al. | |
| 6,771,994 B2 | 8/2004 | Kiani et al. | |
| 6,950,687 B2 | 9/2005 | Al-Ali | |
| 6,985,762 B2 | 1/2006 | Brashears et al. | |
| 6,987,994 B1 | 1/2006 | Mortz | |
| 7,047,054 B2 | 5/2006 | Benni | |
| 7,130,671 B2 | 10/2006 | Baker, Jr. et al. | |
| 7,313,427 B2 | 12/2007 | Benni | |
| 7,457,652 B2 | 11/2008 | Porges et al. | |
| 7,471,969 B2 | 12/2008 | Diab et al. | |
| 2003/0139656 A1 | 7/2003 | Kiani et al. | |
| 2004/0158134 A1 | 8/2004 | Diab et al. | |
| 2004/0158135 A1 | 8/2004 | Baker et al. | |
| 2007/0208235 A1 | 9/2007 | Besson et al. | |

(Continued)

FOREIGN PATENT DOCUMENTS

WO WO9843071 10/1998

*Primary Examiner* — Tse Chen
*Assistant Examiner* — Marjan Fardanesh

(57) ABSTRACT

A physiological monitoring system may determine a probe-off condition. A physiological sensor may receive a light signal including one or more wavelengths of light. The received light signal may be processed to obtain a light signal corresponding to an ambient light signal and a light signal corresponding to an emitted light signal and the ambient light signal. The signals may be analyzed to identify an inverse effect. The system may determine whether the physiological sensor is properly positioned based on the identification of an inverse effect.

12 Claims, 10 Drawing Sheets

(56) References Cited

U.S. PATENT DOCUMENTS

| | | |
|---|---|---|
| 2008/0039699 A1 | 2/2008 | Neumann |
| 2008/0221426 A1 | 9/2008 | Baker et al. |
| 2010/0094106 A1 | 4/2010 | Kiani |
| 2010/0094107 A1 | 4/2010 | Lamego |
| 2011/0237914 A1 | 9/2011 | Lamego et al. |
| 2012/0029310 A1 | 2/2012 | Paquet et al. |

METHODS AND SYSTEMS FOR DETERMINING A PROBE-OFF CONDITION IN A MEDICAL DEVICE

The present disclosure relates to determining a sensor condition, and more particularly relates to determining a dynamic probe-off condition in a pulse oximeter or other medical device.

SUMMARY

Methods and systems are provided for determining whether a physiological sensor is properly positioned on a subject.

A physiological sensor may receive a detected a light signal. The light signal may be processed to obtain a first signal corresponding to ambient light. The light signal may be processed to obtain a second signal corresponding to an emitted photonic signal and ambient light. An inverse effect may be identified based on the first signal and the second signal. It may be determined that the physiological sensor is not properly positioned based on the identification of an inverse effect. An improperly positioned sensor may be in a probe-off condition. In some embodiments, an inverse effect may be identified as opposite behavior in the first light signal and a difference signal, where the difference signal is determined by subtracting the second signal from the first signal.

In some embodiments, a weight may be determined based on the first and second signals. In addition, a count may be determined based on the presence and absence of an inverse effect in the signals. A metric may be determined based on the product of the count and the weight. The metric may be compared to a threshold to identify an inverse effect. In some embodiments, a flag may be set when an inverse effect is identified.

BRIEF DESCRIPTION OF THE FIGURES

The above and other features of the present disclosure, its nature and various advantages will be more apparent upon consideration of the following detailed description, taken in conjunction with the accompanying drawings in which.

DETAILED DESCRIPTION OF THE FIGURES

Figure 1:
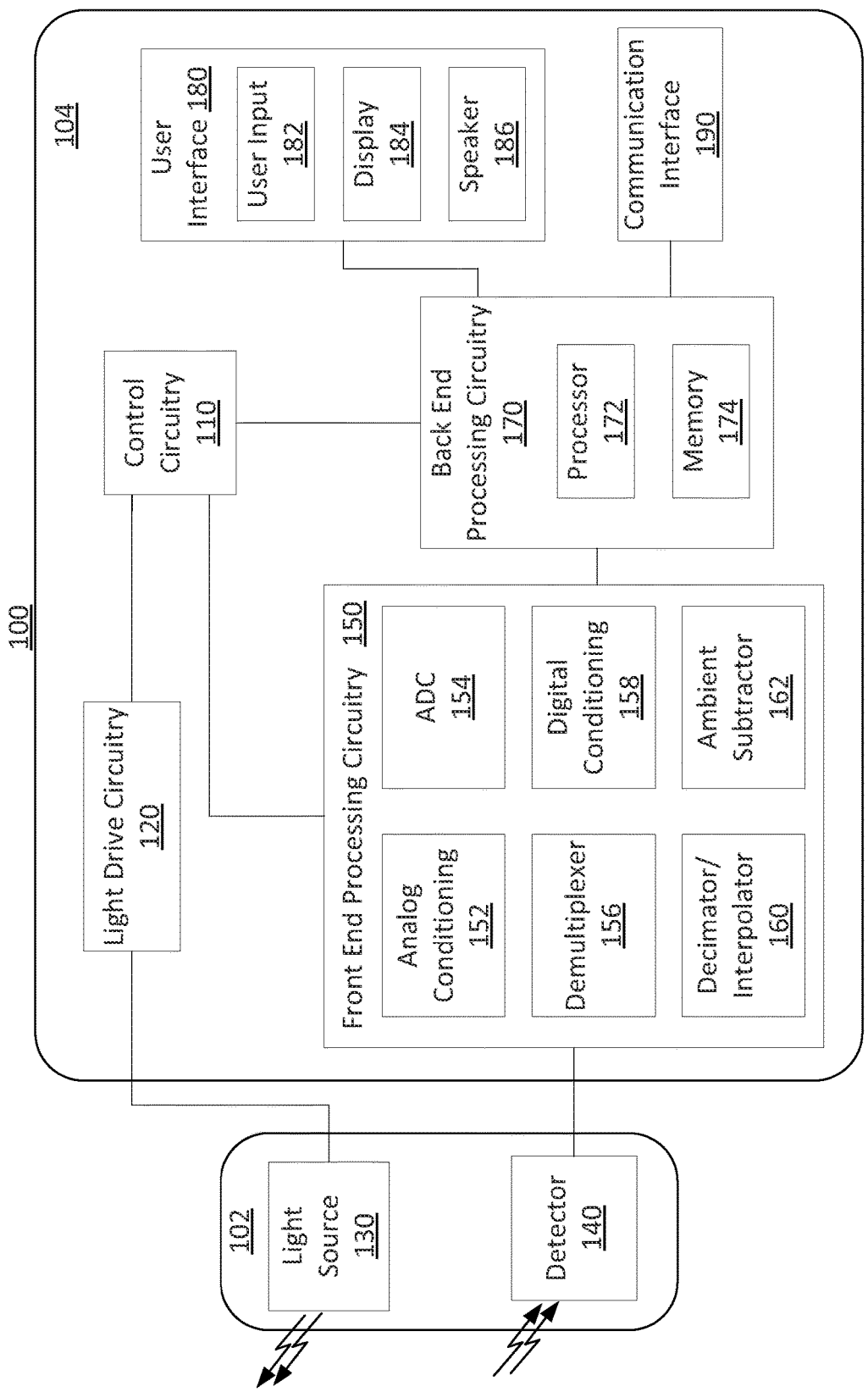
FIG. 1 is a block diagram of an illustrative physiological monitoring system in accordance with some embodiments of the present disclosure.

The present disclosure is directed towards determining a probe-off condition in a medical device. A physiological monitoring system may monitor one or more physiological parameters of a patient, typically using one or more physiological sensors. For example, the physiological monitoring system may include a pulse oximeter. The system may include, for example, a light source and a photosensitive detector. In some embodiments, a sensor may be attached to a target area of a patient. For example, the sensor may be attached using an adhesive, a strap, a band, elastic, any other suitable attachment, or any combination thereof. In some embodiments, the sensor may be located proximate to a desired structural element. For example, a sensor may be held near to the radial artery using a wrist strap. In another example, a sensor may be held near to the blood vessels of the forehead using an adhesive, tape, a headband strap, any other suitable attachment, or any combination thereof. In a further example, a sensor may be held near the blood vessels on a fingertip using an adhesive, tape, or mechanical clip.

In some embodiments, the system may determine a probe-off condition. As used herein, the probe-off condition may include any condition where the sensor is fully or partially detached or moved from the desired target area of the subject. A probe-off condition may include a condition where an adhesive coupling the sensor to the subject has fully or partially failed. A probe-off condition may include a condition where a sensor held with a strap or band has loosened, shifted, slid, moved, detached, repositioned in any other unsuitable arrangement, or any combination thereof. For example, a sensor held by an adhesive to the forehead of a subject may fully or partially separate due to an adhesive failure, resulting in a probe-off condition. In another example, a sensor held proximal to the radial artery at the wrist of a subject by a strap or band may shift out of position, resulting in a probe-off position. It will be understood that the probe-off conditions described herein are merely exemplary and that any suitable undesirable positioning of the sensor may result in a probe-off condition. It will also be understood that the particular arrangement of a probe-off condition may dependent upon the configuration and type of probe.

The probe-off condition may be determined by the system. In some embodiments, the system may use a comparison of the detected ambient signal and a detected light signal to determine a probe-off condition by identifying an inverse effect. The inverse effect may include a dynamic condition where the probe is moving relative to a reflective surface and/or a light source.

As will be described in detail below, a detected ambient signal may include information related to the amount of light a detector receives when one or more associated light sources are in an "off" state. Detected ambient signals may be time division multiplexed in a drive pulse modulation technique. In some embodiments where a detector receives light from light sources coupled to the system and from light sources not coupled to the system, the detected ambient signal may include the light from the light sources not coupled to the system. Ambient light sources may include sunlight, incandescent room lights, fluorescent room lights, fireplaces, candles, naked flames, LED room lights, instrument panel lighting, heat sources, any other suitable light sources not intended for determining a physiological parameter, or any combination thereof. It will be understood that heat sources may generate non-visible IR light that may be detected by the system. It will be understood that any visible or non-visible source of electromagnetic radiation may be included in the detected ambient signal including, for example, radio waves, microwave, IR, visible, UV, X-ray, gamma ray. In some arrangements, the detected ambient signal may include decaying LED light from the system light sources. For example, it may take a particular amount of time for the light output from a light source to decrease to zero following the light drive signal being switched off. A portion of this emitted light may be included in the detected ambient signal. In some arrangements, the detected ambient signal may not contain physiological information.

As will be described in detail below, a detected light signal may include information related to the amount of light a detector receives when one or more associated light sources are in an "on" state. In some embodiments where a detector receives light from light sources coupled to the system and from light sources not coupled to the system, the detected light signal may include light from both sources. Detected light signals may be time division multiplexed in a drive pulse modulation technique. In some embodiments, a detected ambient signal may be subtracted from a detected light signal to determine a pulsatile amplitude signal. In some embodiments, a detected light signal baseline may be identified based on the detected light signal and the detected ambient signal.

In some embodiments, a sensor may be configured to limit the amount of ambient light received by a detector. For example, a detector may be held close to and facing the skin. A detector may include a light blocking material between the detector and any ambient light sources, to prevent or reduce ambient light from reaching the detector. In a further example, a system may include other suitable shields, optics, filters, arrangements, or any combination thereof, to reduce ambient light signals received by the receiver. In some embodiments, the particular arrangement of light blocking structures or material may depend on the type of probe. For example, a forehead probe may include a relatively flat light blocking structure, while a fingertip probe may include a light blocking structure that encircles the finger. It will be understood, however, that many clinical settings include relatively bright light sources and the ambient light signals received by the detector may not be fully blocked when the sensor is positioned as desired. Similarly, fully shielding ambient light may be more difficult for a forehead sensor than, for example, a fingertip sensor.

In some embodiments, for example, with a fingertip sensor where light may be generated by the system on one side of a finger and detected on the opposite side of a finger, removing the detector from a finger (i.e., a probe-off condition) may result in a large portion of the generated light being received by the sensor, rather than a portion of the light being attenuated by interacting with the tissue of the subject. This very high signal level may be determined as a probe-off condition by the system.

In some embodiments, for example, with a forehead sensor, a probe-off condition may not result in a relatively high detected signal level. A forehead sensor may include a light source placed relatively close to a detector on the forehead of a patient using tape, an adhesive, a band encircling the skull, any other suitable arrangement, or any combination thereof. The light source and detector may be arranged such that a portion of the light emitted from the light source interacts with, and is partially attenuated by, the tissue of the subject and is detected by the detector. The light source may be pulsed, such that an ambient signal is detected by the detector between the pulses, and a light signal detected during the pulses includes both the ambient and the desired light. In determining a physiological parameter, the detected ambient signal may be, for example, subtracted from the total signal to generate a pulsatile amplitude signal. The detected ambient signal, the detected light signal, or the relationship between signals may exhibit certain characteristic behavior during a probe-off condition. For example, high signal levels, low signal levels, positive correlations between signals, negative correlations between signals, offset correlations between signals, any other suitable relationships, or any combination thereof may be used by the system to identify a probe-off condition.

In some embodiments, the system may compare a first signal level to a second signal level. For example, a level or trend of the detected ambient signal may be compared to a level or trend of a detected light signal (e.g., an IR signal. In some embodiments, the detected light signal may include light from a red light emitting diode, an infrared light emitting diode, any other suitable light emitter, or any combination thereof. In some embodiments, the detected light signal may include ambient light information, while in some embodiments ambient light information may be removed or subtracted.

In some embodiments, the system may identify particular signal behavior in comparing two or more signals and that behavior may be identified as being indicative of a probe-off condition. The following embodiments are directed primarily towards the signals detected by forehead or similar reflective sensors, where in a detached position the emitter may not be directed towards the detector. It will be understood that this arrangement is merely exemplary and that the techniques described herein may be modified for other sensor arrangements, for example, transmission based fingertip or earlobe sensors.

In some embodiments, the system may identify an inverse effect. The inverse effect may include a signal behavior where the detected ambient signal and a detected light signal vary inversely with respect to each other. For example in certain conditions where an inverse effect may be present, an IR component of a signal may increase simultaneously with an ambient component signal decreasing. The system may identify this behavior as being indicative of a probe-off condition.

In some embodiments where a probe is removed and is situated near a reflective surface, an inverse effect may occur. The detected light signal amplitude, for example an IR signal with the ambient component subtracted, may increase in amplitude due to an increase in the amount of light from the emitters being reflected by the reflective surface and received by the detector. Concurrently, the amplitude of the detected ambient signal, detected while the emitters are off, may decrease due to shading effects by the reflective surface. Thus in some embodiments, as a sensor is brought closer to a reflective surface, the detected ambient signal may decrease due to shading effects while the detected light signal increases due to reflection effects. Similarly, as a sensor is moved further from a reflective surface, the detected ambient signal may increase and the detected light signal may decrease. For example, a sensor in a probe-off condition may move with relation to a reflective surface if it is hanging detached from a patient in a clinical situation and swinging due to air currents or patient motion. In some embodiments, identification of an inverse effect may require a particular amount of ambient light. For example, an inverse effect may only be identified in an illuminated environment.

The system may identify this inverse effect using a metric-based calculation, a Lissajous technique, covariance or other statistical techniques, any other suitable technique, or any combination thereof. In some embodiments, identification of an inverse effect may be combined with other techniques for identifying a probe-off condition. For example, a system may identify high detected ambient signal levels, mimicking or following of two or more signals, signal flatness, high signal levels, low signal levels, any other suitable condition, or any combination thereof. Multiple signals may be combined using any suitable algorithmic technique, logic technique, weighted technique, sequence-dependent technique, any other suitable technique, or any combination thereof.

The foregoing techniques may be implemented in a medical device such as an oximeter. An oximeter may determine the oxygen saturation of an analyzed tissue. One common type of oximeter is a pulse oximeter, which may non-invasively measure the oxygen saturation of a patient's blood (as opposed to measuring oxygen saturation directly by analyzing a blood sample taken from the patient). Pulse oximeters may be included in patient monitoring systems that measure and display various blood flow characteristics including, but not limited to, the oxygen saturation of hemoglobin in arterial blood. Such patient monitoring systems may also measure and display additional physiological parameters, such as a patient's pulse rate and blood pressure.

An oximeter may include a light sensor that is placed at a site on a patient, typically a fingertip, toe, forehead or earlobe, or in the case of a neonate, across a foot or hand. The oximeter may use a light source to pass light through blood perfused tissue and photoelectrically sense the absorption of the light in the tissue. In addition, locations which are not typically understood to be optimal for pulse oximetry serve as suitable sensor locations for the blood pressure monitoring processes described herein, including any location on the body that has a strong pulsatile arterial flow. For example, additional suitable sensor locations include, without limitation, the neck to monitor carotid artery pulsatile flow, the wrist to monitor radial artery pulsatile flow, the inside of a patient's thigh to monitor femoral artery pulsatile flow, the ankle to monitor tibial artery pulsatile flow, and around or in front of the ear. Suitable sensors for these locations may include sensors for sensing absorbed light based on detecting reflected light. In all suitable locations, for example, the oximeter may measure the intensity of light that is received at the light sensor as a function of time. The oximeter may also include sensors at multiple locations. A signal representing light intensity versus time or a mathematical manipulation of this signal (e.g., a scaled version thereof, a log taken thereof, a scaled version of a log taken thereof, etc.) may be referred to as the photoplethysmograph (PPG) signal. In addition, the term "PPG signal," as used herein, may also refer to an absorption signal (i.e., representing the amount of light absorbed by the tissue) or any suitable mathematical manipulation thereof. The light intensity or the amount of light absorbed may then be used to calculate any of a number of physiological parameters, including an amount of a blood constituent (e.g., oxyhemoglobin) being measured as well as a pulse rate and when each individual pulse occurs.

In some embodiments, the photonic signal interacting with the tissue is selected to be of one or more wavelengths that are attenuated by the blood in an amount representative of the blood constituent concentration. Red and infrared (IR) wavelengths may be used because it has been observed that highly oxygenated blood will absorb relatively less red light and more IR light than blood with a lower oxygen saturation. By comparing the intensities of two wavelengths at different points in the pulse cycle, it is possible to estimate the blood oxygen saturation of hemoglobin in arterial blood.

The system may process data to determine physiological parameters using techniques well known in the art. For example, the system may determine blood oxygen saturation using two wavelengths of light and a ratio-of-ratios calculation. The system also may identify pulses and determine pulse amplitude, respiration, blood pressure, other suitable parameters, or any combination thereof, using any suitable calculation techniques. In some embodiments, the system may use information from external sources (e.g., tabulated data, secondary sensor devices) to determine physiological parameters.

In some embodiments, a light drive modulation may be used. For example, a first light source may be turned on for a first drive pulse, followed by an off period, followed by a second light source for a second drive pulse, followed by an off period. The first and second drive pulses may be used to determine physiological parameters. The off periods may be used to determine detected ambient signal levels, reduce overlap of the light drive pulses, allow time for light sources to stabilize, allow time for the detected light signals to stabilize, reduce heating effects, reduce power consumption, for any other suitable reason, or any combination thereof.

It will be understood that the probe-off techniques described herein are not limited to pulse oximeters and may be applied to any suitable medical and non-medical devices. For example, the system may include probes for regional saturation (rSO2), respiration rate, respiration effort, continuous non-invasive blood pressure, saturation pattern detection, fluid responsiveness, cardiac output, any other suitable clinical parameter, or any combination thereof. Probes may be used with a pulse oximeter, a general purpose medical monitor, any other suitable medical device, or any combination thereof. In some embodiments, the probe-off identification techniques described herein may be applied to analysis of light levels where an ambient or dark signal is detected.

The following description and accompanying FIGS. 1-10 provide additional details and features of some embodiments of determining a sensor condition in a medical device.

FIG. 1 is a block diagram of an illustrative physiological monitoring system 100 in accordance with some embodiments of the present disclosure. System 100 may include a sensor 102 and a monitor 104 for generating and processing physiological signals of a subject. In some embodiments, sensor 102 and monitor 104 may be part of an oximeter.

Sensor 102 of physiological monitoring system 100 may include light source 130 and detector 140. Light source 130 may be configured to emit photonic signals having one or more wavelengths of light (e.g. Red and IR) into a subject's tissue. For example, light source 130 may include a Red light emitting light source and an IR light emitting light source, e.g. Red and IR light emitting diodes (LEDs), for emitting light into the tissue of a subject to generate physiological signals. In one embodiment, the Red wavelength may be between about 600 nm and about 700 nm, and the IR wavelength may be between about 800 nm and about 1000 nm. It will be understood that light source 130 may include any number of light sources with any suitable characteristics. In embodiments where an array of sensors is used in place of single sensor 102, each sensor may be configured to emit a single wavelength. For example, a first sensor may emit only a Red light while a second may emit only an IR light.

It will be understood that, as used herein, the term "light" may refer to energy produced by radiative sources and may include one or more of ultrasound, radio, microwave, millimeter wave, infrared, visible, ultraviolet, gamma ray or X-ray electromagnetic radiation. As used herein, light may also include any wavelength within the radio, microwave, infrared, visible, ultraviolet, or X-ray spectra, and that any suitable wavelength of electromagnetic radiation may be appropriate for use with the present techniques. Detector 140 may be chosen to be specifically sensitive to the chosen targeted energy spectrum of light source 130.

In some embodiments, detector 140 may be configured to detect the intensity of light at the Red and IR wavelengths. In some embodiments, an array of sensors may be used and each sensor in the array may be configured to detect an intensity of a single wavelength. In operation, light may enter detector 140 after passing through the subject's tissue. Detector 140 may convert the intensity of the received light into an electrical signal. The light intensity may be directly related to the absorbance and/or reflectance of light in the tissue. That is, when more light at a certain wavelength is absorbed, scattered, or reflected, less light of that wavelength is received from the tissue by detector 140. After converting the received light to an electrical signal, detector 140 may send the detection signal to monitor 104, where the detection signal may be processed and physiological parameters may be determined (e.g., based on the absorption of the Red and IR wavelengths in the subject's tissue). In some embodiments, the detection signal may be preprocessed by sensor 102 before being transmitted to monitor 104.

In the embodiment shown, monitor 104 includes control circuitry 110, light drive circuitry 120, front end processing circuitry 150, back end processing circuitry 170, user interface 180, and communication interface 190. Monitor 104 may be communicatively coupled to sensor 102.

Control circuitry 110 may be coupled to light drive circuitry 120, front end processing circuitry 150, and back end processing circuitry 170, and may be configured to control the operation of these components. In some embodiments, control circuitry 110 may be configured to provide timing control signals to coordinate their operation. For example, light drive circuitry 120 may generate a light drive signal, which may be used to turn on and off the light source 130, based on the timing control signals. The front end processing circuitry 150 may use the timing control signals to operate synchronously with light drive circuitry 120. For example, front end processing circuitry 150 may synchronize the operation of an analog-to-digital converter and a demultiplexer with the light drive signal based on the timing control signals. In addition, the back end processing circuitry 170 may use the timing control signals to coordinate its operation with front end processing circuitry 150.

Light drive circuitry 120, as discussed above, may be configured to generate a light drive signal that is provided to light source 130 of sensor 102. The light drive signal may, for example, control the intensity of light source 130 and the timing of when light source 130 is turned on and off. When light source 130 is configured to emit two or more wavelengths of light, the light drive signal may be configured to control the operation of each wavelength of light. The light drive signal may comprise a single signal or may comprise multiple signals (e.g., one signal for each wavelength of light). An illustrative light drive signal is shown in FIG. 2A.

Figure 2A:
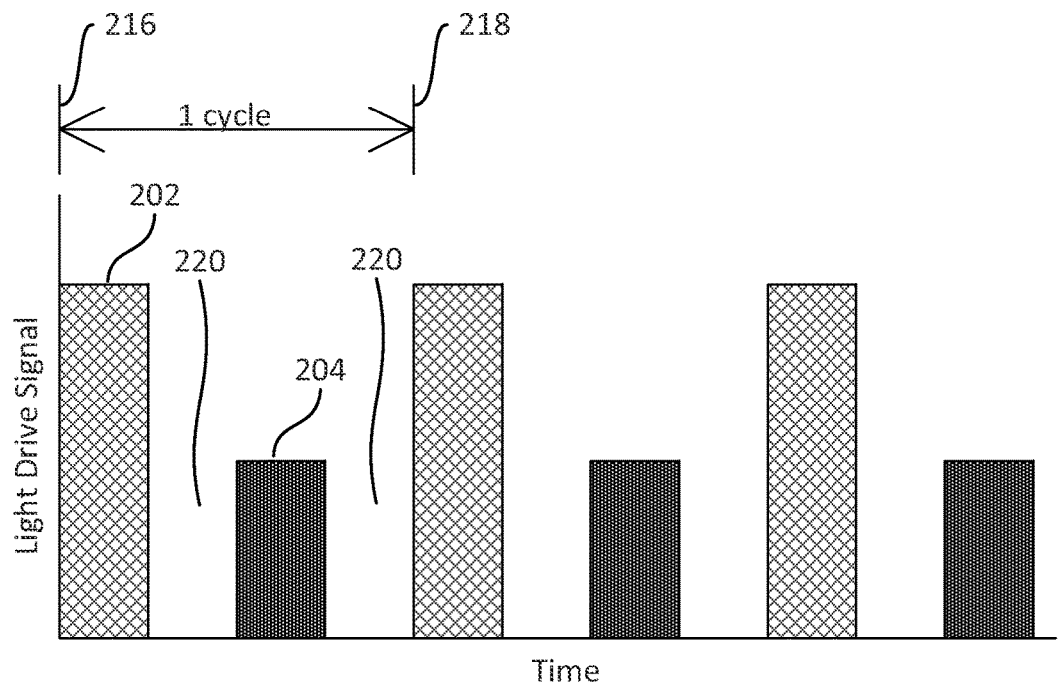
FIG. 2A shows an illustrative plot of a light drive signal including a red light drive pulse and an IR light drive pulse in accordance with some embodiments of the present disclosure.

FIG. 2A shows an illustrative plot of a light drive signal including red light drive pulse 202 and IR light drive pulse 204 in accordance with some embodiments of the present disclosure. Drive pulses 202, and 204 may be generated by light drive circuitry 120 under the control of control circuitry 110. As used herein, drive pulses may refer to switching power or other components on and off, high and low output states, high and low values within a continuous modulation, other suitable relatively distinct states, or any combination thereof. The light drive signal may be provided to light source 130, including red drive pulse 202 and IR drive pulse 204 to drive red and IR light emitters, respectively, within light source 130. Red drive pulse 202 may have a higher amplitude than IR drive 204 since red LEDs may be less efficient than IR LEDs at converting electrical energy into light energy. In some embodiments, the output levels may be the equal, may be corrected or otherwise adjusted based on the nonlinearity of emitters and the detector, may be modulated in any other suitable technique, or any combination thereof. Additionally, red light may be absorbed and scattered more than IR light when passing through perfused tissue. When the red and IR light sources are driven in this manner they emit pulses of light at their respective wavelengths into the tissue of a subject in order generate physiological signals that physiological monitoring system 100 may process to calculate physiological parameters. It will be understood that the light drive amplitudes of FIG. 2A are merely exemplary any that any suitable amplitudes or combination of amplitudes may be used, and may be based on the light sources, the subject tissue, the determined physiological parameter, modulation techniques, power sources, any other suitable criteria, or any combination thereof.

The light drive signal of FIG. 2A may also include "off" periods 220 between the Red and IR light drive pulse. "Off" periods 220 are periods during which no drive current may be applied to light source 130. "Off" periods 220 may be provided, for example, to prevent overlap of the emitted light, since light source 130 may require time to turn completely on and completely off. Similarly, the signal from detector 140 may require time to decay completely to a final state after light source 130 is switched off. The period from time 216 to time 218 may be referred to as a drive cycle, which includes four segments: a Red light drive pulse 202, followed by an "off" period 220, followed by an IR light drive pulse 204, and followed by an "off" period 220. After time 218, the drive cycle may be repeated (e.g., as long as a light drive signal is provided to light source 130). It will be understood that the starting point of the drive cycle is merely illustrative and that the drive cycle can start at any location within FIG. 2A, provided the cycle spans two drive pulses and two "off" periods. Thus, each Red light drive pulse 202 and each IR drive pulse 204 may be understood to be surrounded by two "off" periods 220. "Off" periods may also be referred to as dark periods, in that the emitters are dark during that period.

Referring back to FIG. 1, front end processing circuitry 150 may receive a detection signal from detector 140 and provide one or more processed signals to back end processing circuitry 170. The term "detection signal," as used herein, may refer to any of the signals generated within front end processing circuitry 150 as it processes the output signal of detector 140. Front end processing circuitry 150 may perform various analog and digital processing of the detector signal. One suitable detector signal that may be received by front end processing circuitry 150 is shown in FIG. 2B.

Figure 2B:
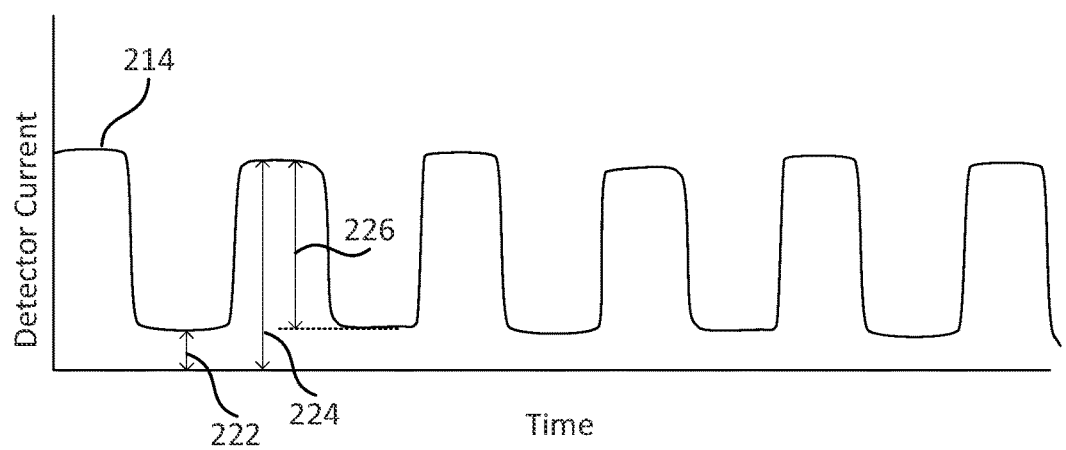
FIG. 2B shows an illustrative plot of a detector signal that may be generated by a sensor in accordance with some embodiments of the present disclosure.

FIG. 2B shows an illustrative plot of detector current waveform 214 that may be generated by a sensor in accordance with some embodiments of the present disclosure. The peaks of detector current waveform 214 may represent current signals provided by a detector, such as detector 140 of FIG. 1, when light is being emitted from a light source. The amplitude of detector current waveform 214 may be proportional to the light incident upon the detector. The peaks of detector current waveform 214 may be synchronous with drive pulses driving one or more emitters of a light source, such as light source 130 of FIG. 1. For example, detector current waveform 214 may be generated in response to a light source being driven by the light drive signal of FIG. 2A. The valleys of detector current waveform 214 may be synchronous with periods of time during which no light is being emitted by the light source. While no light is being emitted by a light source during the valleys, detector current waveform 214 may not fall all of the way to zero. Rather, ambient signal 222 may be present in the detector waveform. In some embodiments, ambient signal 222 may be used to determine a probe-off condition. In some embodiments, ambient signal 222 may be removed from a processed signal to improve determination of physiological parameters.

In some embodiments, the system may determine pulsatile amplitude 226 and peak amplitude signal 224 in detector current waveform 214. For example, pulsatile amplitude signal 226 may be determined by subtracting ambient signal 222 from peak amplitude signal 224. In some embodiments, pulsatile amplitude signal 226 may represent an alternating or AC signal superimposed on a constant or DC offset, where the constant offset is ambient signal 222. In some embodiments, the system may determine average values for each signal and then determine the difference. In some embodiments, the system may determine the values for each pulse in detector current waveform 214, and then average those values together. It will be understood that the aforementioned is merely exemplary and that the system may determine pulsatile amplitude signal 226 by any suitable technique.

Referring back to FIG. 1, front end processing circuitry 150, which may receive a detection signal, such as detector current waveform 214, may include analog conditioning 152, analog-to-digital converter 154, demultiplexer 156, digital conditioning 158, decimator/interpolator 160, and ambient subtractor 162.

In some embodiments, front end processing circuitry 150 may contain another analog-to-digital converter (not shown) configured to sample the unprocessed detector signal. This signal may be used to detect changes in the ambient light level without applying the signal condition and other steps that may improve the quality of determined physiological parameters but may reduce the amount of information regarding a probe-off condition.

Analog conditioning 152 may perform any suitable analog conditioning of the detector signal. The conditioning performed may include any type of filtering (e.g., low pass, high pass, band pass, notch, or any other suitable filtering), amplifying, performing an operation on the received signal (e.g., taking a derivative, averaging), performing any other suitable signal conditioning (e.g., converting a current signal to a voltage signal), or any combination thereof.

The conditioned analog signal may be processed by analog-to-digital converter 154, which may convert the conditioned analog signal into a digital signal. Analog-to-digital converter 154 may operate under the control of control circuitry 110. Analog-to-digital converter 154 may use timing control signals from control circuitry 110 to determine when to sample the analog signal. Analog-to-digital converter 154 may be any suitable type of analog-to-digital converter of sufficient resolution to enable a physiological monitor to accurately determine physiological parameters.

Demultiplexer 156 may operate on the analog or digital form of the detector signal to separate out different components of the signal. For example, detector current waveform 214 of FIG. 2B includes a Red component, an IR component, and at least one ambient component. Demultiplexer 156 may operate on detector current waveform 214 of FIG. 2B to generate a Red signal, an IR signal, a first ambient signal (e.g., corresponding to the ambient component that occurs immediately after the Red component), and a second ambient signal (e.g., corresponding to the ambient component that occurs immediately after the IR component). Demultiplexer 156 may operate under the control of control circuitry 110. For example, demultiplexer 156 may use timing control signals from control circuitry 110 to identify and separate out the different components of the detector signal.

Digital conditioning 158 may perform any suitable digital conditioning of the detector signal. The digital conditioning may include any type of digital filtering of the signal (e.g., low pass, high pass, band pass, notch, or any other suitable filtering), amplifying, performing an operation on the signal, performing any other suitable digital conditioning, or any combination thereof.

Decimator/interpolator 160 may decrease the number of samples in the digital detector signal. For example, decimator/interpolator 160 may decrease the number of samples by removing samples from the detector signal or replacing samples with a smaller number of samples. The decimation or interpolation operation may include or be followed by filtering to smooth the output signal.

Ambient subtractor 162 may operate on the digital signal. In some embodiments, ambient subtractor 162 may remove ambient values from the Red and IR components. In some embodiments, the system may subtract the ambient values from the Red and IR components to generate ambient-corrected Red and IR signals. For example, ambient subtractor 162 may determine a subtraction amount from the ambient signal portion of the detection signal and subtract it from the peak portion of the detection signal in order to reduce the effect of the ambient signal on the peak. For example, in reference to FIG. 2A, a detection signal peak corresponding to red drive pulse 202 may be corrected or otherwise altered by determining the amount of ambient signal during the "off" period 220 preceding red drive pulse 202. The ambient signal amount determined in this manner may be subtracted from the detector peak corresponding to red drive pulse 202. Alternatively, the "off" period 220 after red drive pulse 202 may be used to correct red drive pulse 202 rather than the "off" period 220 preceding it. Additionally, an average of the "off" periods 220 before and after red "on" period 202 may be used. In some embodiments, ambient subtractor 162 may output an ambient signal for further processing. Ambient subtractor 162 may average the ambient signal from multiple "off" periods 220, may apply filters to the ambient signal such as averaging filters, integration filters, delay filters, buffers, counters, any other suitable filters or processing equipment, or any combination thereof.

It will be understood that in some embodiments, ambient subtractor 162 may be omitted. It will also be understood that in some embodiments, the system may not subtract the ambient contribution of the signal. It will also be understood that the functions of demultiplexer 154 and ambient subtractor 162 may be complementary, overlapping, combined into a signal function, combined or separated in any suitable arrangement, or any combination thereof. For example, the received light signal may include an ambient signal, an IR light signal, and a red light signal. The system may use any suitable arrangement of demultiplexer 154 and ambient subtractor 162 to determine or generate any combination of: a red signal, an IR signal, a red ambient signal, an IR ambient signal, an average ambient signal, a red with ambient signal, an IR with ambient signal, any other suitable signal, or any combination thereof.

The components of front end processing circuitry 150 are merely illustrative and any suitable components and combinations of components may be used to perform the front end processing operations.

The front end processing circuitry 150 may be configured to take advantage of the full dynamic range of analog-to-digital converter 154. This may be achieved by applying gain to the detection signal by analog conditioning 152 to map the expected range of the detection signal to the full or close to full output range of analog-to-digital converter 154. The output value of analog-to-digital converter 154, as a function of the total analog gain applied to the detection signal, may be given as Eq. 1:

$$ADC \text{ Value} = \text{Total Analog Gain} \times [\text{Ambient Light} + \text{LED Light}] \quad (1)$$

Ideally, when ambient light is zero and when the light source is off, the analog-to-digital converter 154 will read just above the minimum input value. When the light source is on, the total analog gain may be set such that the output of analog-to-digital converter 154 may read close to the full scale of analog-to-digital converter 154 without saturating. This may allow the full dynamic range of analog-to-digital converter 154 to be used for representing the detection signal, thereby increasing the resolution of the converted signal. In some embodiments, the total analog gain may be reduced by a small amount so that small changes in the light level incident on the detector do not cause saturation of analog-to-digital converter 154.

Back end processing circuitry 170 may include processor 172 and memory 174. Processor 172 may be adapted to execute software, which may include an operating system and one or more applications, as part of performing the functions described herein. Processor 172 may receive and further process physiological signals received from front end processing circuitry 150. For example, processor 172 may determine one or more physiological parameters based on the received physiological signals. Memory 174 may include any suitable computer-readable media capable of storing information that can be interpreted by processor 172. This information may be data or may take the form of computer-executable instructions, such as software applications, that cause the microprocessor to perform certain functions and/or computer-implemented methods. Depending on the embodiment, such computer-readable media may include computer storage media and communication media. Computer storage media may include volatile and non-volatile, removable and non-removable media implemented in any method or technology for storage of information such as computer-readable instructions, data structures, program modules or other data. Computer storage media may include, but is not limited to, RAM, ROM, EPROM, EEPROM, flash memory or other solid state memory technology, CD-ROM, DVD, or other optical storage, magnetic cassettes, magnetic tape, magnetic disk storage or other magnetic storage devices, or any other medium which can be used to store the desired information and which can be accessed by components of the system. Back end processing circuitry 170 may be communicatively coupled with use interface 180 and communication interface 190.

User interface 180 may include user input 182, display 184, and speaker 186. User input 182 may include any type of user input device such as a keyboard, a mouse, a touch screen, buttons, switches, a microphone, a joy stick, a touch pad, or any other suitable input device. The inputs received by user input 182 can include information about the subject, such as age, weight, height, diagnosis, medications, treatments, and so forth. In an embodiment, the subject may be a medical patient and display 184 may exhibit a list of values which may generally apply to the patient, such as, for example, age ranges or medication families, which the user may select using user inputs 182. Additionally, display 184 may display, for example, an estimate of a subject's blood oxygen saturation generated by monitor 104 (referred to as an "$SpO_2$" measurement), pulse rate information, respiration rate information, blood pressure, sensor condition, sensor positioning, any other parameters, and any combination thereof. Display 184 may include any type of display such as a cathode ray tube display, a flat panel display such a liquid crystal display or plasma display, or any other suitable display device. Speaker 186 within user interface 180 may provide an audible sound that may be used in various embodiments, such as for example, sounding an audible alarm in the event that a patient's physiological parameters are not within a predefined normal range.

Communication interface 190 may enable monitor 104 to exchange information with external devices. Communications interface 190 may include any suitable hardware, software, or both, which may allow monitor 104 to communicate with electronic circuitry, a device, a network, a server or other workstations, a display, or any combination thereof. Communications interface 190 may include one or more receivers, transmitters, transceivers, antennas, plug-in connectors, ports, communications buses, communications protocols, device identification protocols, any other suitable hardware or software, or any combination thereof. Communications interface 190 may be configured to allow wired communication (e.g., using USB, RS-232, Ethernet, or other standards), wireless communication (e.g., using WiFi, IR, WiMax, BLUETOOTH, UWB, or other standards), or both. For example, communications interface 190 may be configured using a universal serial bus (USB) protocol (e.g., USB 2.0, USB 3.0), and may be configured to couple to other devices (e.g., remote memory devices storing templates) using a four-pin USB standard Type-A connector (e.g., plug and/or socket) and cable. In some embodiments, communications interface 190 may include an internal bus such as, for example, one or more slots for insertion of expansion cards.

It will be understood that the components of physiological monitoring system 100 that are shown and described as separate components are shown and described as such for illustrative purposes only. In some embodiments the functionality of some of the components may be combined in a single component. For example, the functionality of front end processing circuitry 150 and back end processing circuitry 170 may be combined in a single processor system. Additionally, in some embodiments the functionality of some of the components of monitor 104 shown and described herein may be divided over multiple components. For example, some or all of the functionality of control circuitry 110 may be performed in front end processing circuitry 150, in back end processing circuitry 170, or both. In other embodiments, the functionality of one or more of the components may be performed in a different order or may not be required. In some embodiments, all of the components of physiological monitoring system 100 can be realized in processor circuitry.

Figure 3:
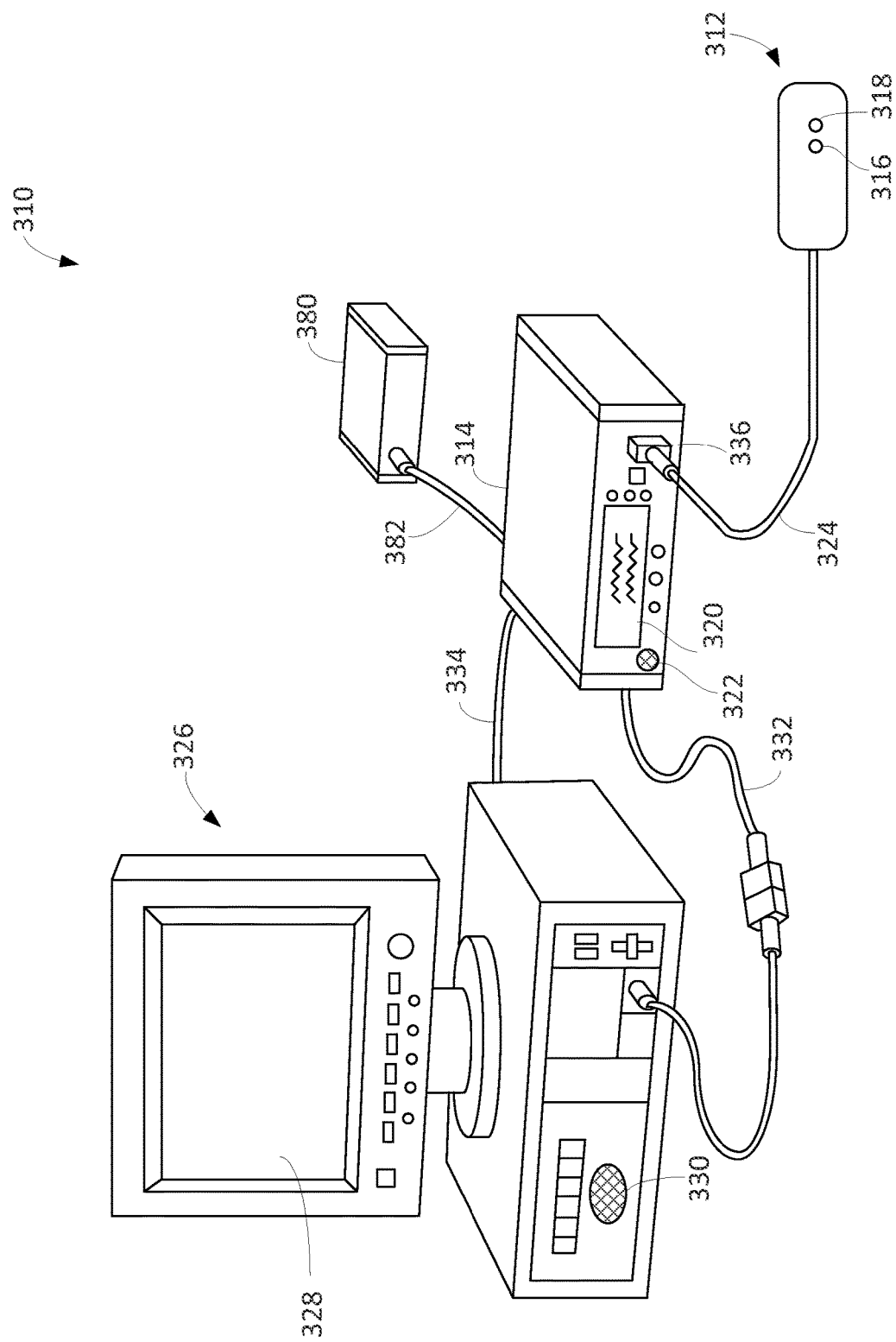
FIG. 3 is a perspective view of an embodiment of a physiological monitoring system in accordance with some embodiments of the present disclosure.

FIG. 3 is a perspective view of an embodiment of a physiological monitoring system 310 in accordance with some embodiments of the present disclosure. In some embodiments, one or more components of physiological monitoring system 310 may include one or more components of physiological monitoring system 100 of FIG. 1. Physiological monitoring system 310 may include sensor unit 312 and monitor 314. In some embodiments, sensor unit 312 may be part of an oximeter. Sensor unit 312 may include one or more light source 316 for emitting light at one or more wavelengths into a subject's tissue. One or more detector 318 may also be provided in sensor unit 312 for detecting the light that is reflected by or has traveled through the subject's tissue. Any suitable configuration of light source 316 and detector 318 may be used. In an embodiment, sensor unit 312 may include multiple light sources and detectors, which may be spaced apart. Physiological monitoring system 310 may also include one or more additional sensor units (not shown) that may, for example, take the form of any of the embodiments described herein with reference to sensor unit 312. An additional sensor unit may be the same type of sensor unit as sensor unit 312, or a different sensor unit type than sensor unit 312 (e.g., a photoacoustic sensor). Multiple sensor units may be capable of being positioned at two or more different locations on a subject's body.

In some embodiments, sensor unit 312 may be connected to monitor 314 as shown. Sensor unit 312 may be powered by an internal power source, e.g., a battery (not shown). Sensor unit 312 may draw power from monitor 314. In another embodiment, the sensor may be wirelessly connected to monitor 314 (not shown). Monitor 314 may be configured to calculate physiological parameters based at least in part on data relating to light emission and acoustic detection received from one or more sensor units such as sensor unit 312. For example, monitor 314 may be configured to determine pulse rate, blood pressure, blood oxygen saturation (e.g., arterial, venous, or both), hemoglobin concentration (e.g., oxygenated, deoxygenated, and/or total), any other suitable physiological parameters, or any combination thereof. In some embodiments, calculations may be performed on the sensor units or an intermediate device and the result of the calculations may be passed to monitor 314. Further, monitor 314 may include display 320 configured to display the physiological parameters or other information about the system. In the embodiment shown, monitor 314 may also include a speaker 322 to provide an audible sound that may be used in various other embodiments, such as for example, sounding an audible alarm in the event that a subject's physiological parameters are not within a predefined normal range or when a sensor is not properly positioned. In some embodiments, physiological monitoring system 310 may include a stand-alone monitor in communication with the monitor 314 via a cable or a wireless network link. In some embodiments, monitor 314 may be implemented as display 184 of FIG. 1.

In some embodiments, sensor unit 312 may be communicatively coupled to monitor 314 via a cable 324 through port 336. Cable 324 may include electronic conductors (e.g., wires for transmitting electronic signals from detector 318), optical fibers (e.g., multi-mode or single-mode fibers for transmitting emitted light from light source 316), any other suitable components, any suitable insulation or sheathing, or any combination thereof. In some embodiments, a wireless transmission device (not shown) or the like may be used instead of or in addition to cable 324. Monitor 314 may include a sensor interface configured to receive physiological signals from sensor unit 312, provide signals and power to sensor unit 312, or otherwise communicate with sensor unit 312. The sensor interface may include any suitable hardware, software, or both, which may be allow communication between monitor 314 and sensor unit 312.

In some embodiments, physiological monitoring system 310 may include calibration device 380. Calibration device 380, which may be powered by monitor 314, a battery, or by a conventional power source such as a wall outlet, may include any suitable calibration device. Calibration device 380 may be communicatively coupled to monitor 314 via communicative coupling 382, and/or may communicate wirelessly (not shown). In some embodiments, calibration device 380 is completely integrated within monitor 314. In some embodiments, calibration device 380 may include a manual input device (not shown) used by an operator to manually input reference signal measurements obtained from some other source (e.g., an external invasive or non-invasive physiological measurement system).

In the illustrated embodiment, physiological monitoring system 310 includes a multi-parameter physiological monitor 326. The monitor 326 may include a cathode ray tube display, a flat panel display (as shown) such as a liquid crystal display (LCD) or a plasma display, or may include any other type of monitor now known or later developed. Multi-parameter physiological monitor 326 may be configured to calculate physiological parameters and to provide a display 328 for information from monitor 314 and from other medical monitoring devices or systems (not shown). For example, multi-parameter physiological monitor 326 may be configured to display an estimate of a subject's blood oxygen saturation and hemoglobin concentration generated by monitor 314. Multi-parameter physiological monitor 326 may include a speaker 330.

Monitor 314 may be communicatively coupled to multi-parameter physiological monitor 326 via a cable 332 or 334 that is coupled to a sensor input port or a digital communications port, respectively and/or may communicate wirelessly (not shown). In addition, monitor 314 and/or multi-parameter physiological monitor 326 may be coupled to a network to enable the sharing of information with servers or other workstations (not shown). Monitor 314 may be powered by a battery (not shown) or by a conventional power source such as a wall outlet.

In some embodiments, all or some of monitor 314 and multi-parameter physiological monitor 326 may be referred to collectively as processing equipment.

Figure 4:
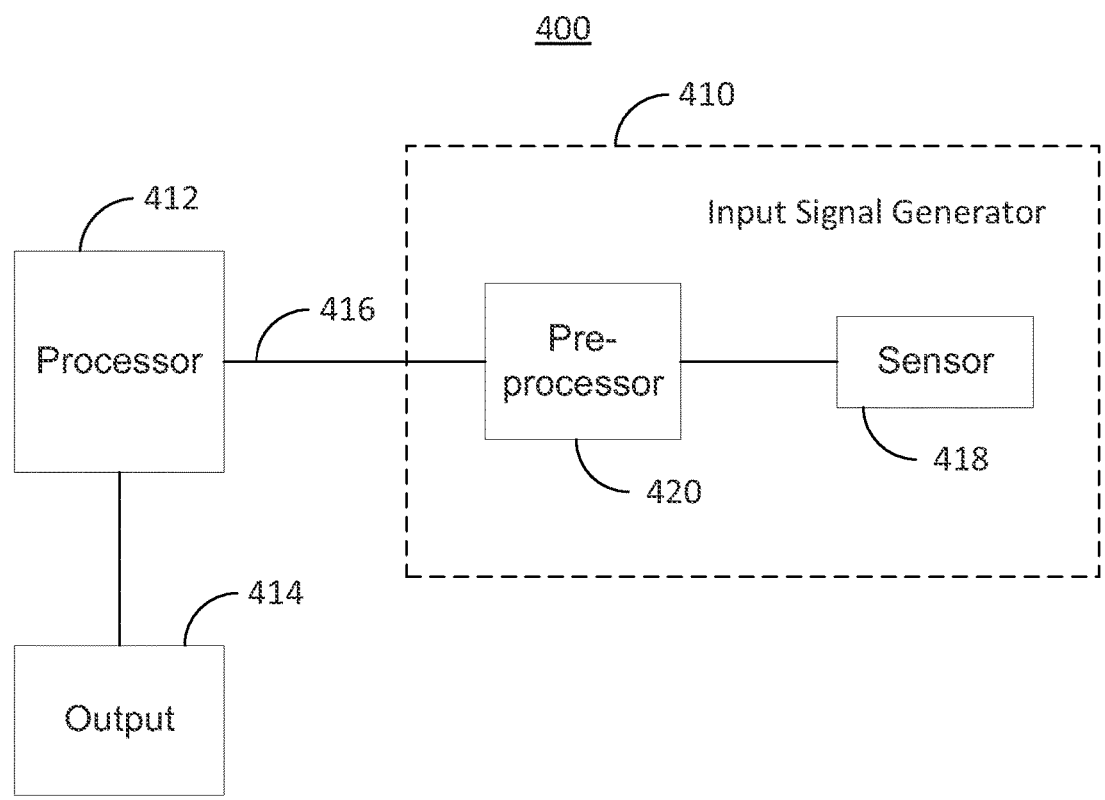
FIG. 4 shows an illustrative signal processing system in accordance with an embodiment that may implement the signal processing techniques described herein.

FIG. 4 shows illustrative signal processing system 400 in accordance with an embodiment that may implement the signal processing techniques described herein. Signal processing system 400 includes input signal generator 410, processor 412 and output 414. In the illustrated embodiment, input signal generator 410 may include pre-processor 420 coupled to sensor 418. As illustrated, input signal generator 410 generates an input signal 416. In some embodiments, input signal 416 may include one or more intensity signals based on a detector output. In some embodiments, pre-processor 420 may be an oximeter and input signal 416 may be a PPG signal. In an embodiment, pre-processor 420 may be any suitable signal processing device and input signal 416 may include PPG signals and one or more other physiological signals, such as an electrocardiogram (ECG) signal. It will be understood that input signal generator 410 may include any suitable signal source, signal generating data, signal generating equipment, or any combination thereof to produce signal 416. Signal 416 may be a single signal, or may be multiple signals transmitted over a single pathway or multiple pathways.

Pre-processor 420 may apply one or more signal processing operations to the signal generated by sensor 418. For example, pre-processor 420 may apply a pre-determined set of processing operations to the signal provided by sensor 418 to produce input signal 416 that can be appropriately interpreted by processor 412, such as performing A/D conversion. In some embodiments, A/D conversion may be performed by processor 412. Pre-processor 420 may also perform any of the following operations on the signal provided by sensor 418: reshaping the signal for transmission, multiplexing the signal, modulating the signal onto carrier signals, compressing the signal, encoding the signal, and filtering the signal. In some embodiments, pre-processor 420 may include a current-to-voltage converter (e.g., to convert a photocurrent into a voltage), an amplifier, a filter, and A/D converter, a de-multiplexer, any other suitable pre-processing components, or any combination thereof. In some embodiments, pre-processor 420 may include one or more components from front end processing circuitry 150 of FIG. 1.

In some embodiments, signal 416 may include PPG signals corresponding to one or more light frequencies, such as an IR PPG signal and a Red PPG signal, and ambient light. In some embodiments, signal 416 may include signals measured at one or more sites on a subject's body, for example, a subject's finger, toe, ear, arm, or any other body site. In some embodiments, signal 416 may include multiple types of signals (e.g., one or more of an ECG signal, an EEG signal, an acoustic signal, an optical signal, a signal representing a blood pressure, and a signal representing a heart rate). Signal 416 may be any suitable biosignal or any other suitable signal.

In some embodiments, signal 416 may be coupled to processor 412. Processor 412 may be any suitable software, firmware, hardware, or combination thereof for processing signal 416. For example, processor 412 may include one or more hardware processors (e.g., integrated circuits), one or more software modules, computer-readable media such as memory, firmware, or any combination thereof. Processor 412 may, for example, be a computer or may be one or more chips (i.e., integrated circuits). Processor 412 may, for example, include an assembly of analog electronic components. Processor 412 may calculate physiological information. For example, processor 412 may compute one or more of a pulse rate, respiration rate, blood pressure, or any other suitable physiological parameter. Processor 412 may perform any suitable signal processing of signal 416 to filter signal 416, such as any suitable band-pass filtering, adaptive filtering, closed-loop filtering, any other suitable filtering, and/or any combination thereof. Processor 412 may also receive input signals from additional sources (not shown). For example, processor 412 may receive an input signal containing information about treatments provided to the subject. Additional input signals may be used by processor 412 in any of the calculations or operations it performs in accordance with processing system 400.

In some embodiments, all or some of pre-processor 420, processor 412, or both, may be referred to collectively as processing equipment.

Processor 412 may be coupled to one or more memory devices (not shown) or incorporate one or more memory devices such as any suitable volatile memory device (e.g., RAM, registers, etc.), non-volatile memory device (e.g., ROM, EPROM, magnetic storage device, optical storage device, flash memory, etc.), or both. The memory may be used by processor 412 to, for example, store fiducial information or initialization information corresponding to physiological monitoring. In some embodiments, processor 412 may store physiological measurements or previously received data from signal 416 in a memory device for later retrieval. In some embodiments, processor 412 may store calculated values, such as a pulse rate, a blood pressure, a blood oxygen saturation, a fiducial point location or characteristic, an initialization parameter, or any other calculated values, in a memory device for later retrieval.

Processor 412 may be coupled to output 414. Output 414 may be any suitable output device such as one or more medical devices (e.g., a medical monitor that displays various physiological parameters, a medical alarm, or any other suitable medical device that either displays physiological parameters or uses the output of processor 412 as an input), one or more display devices (e.g., monitor, PDA, mobile phone, any other suitable display device, or any combination thereof), one or more audio devices, one or more memory devices (e.g., hard disk drive, flash memory, RAM, optical disk, any other suitable memory device, or any combination thereof), one or more printing devices, any other suitable output device, or any combination thereof.

It will be understood that system 400 may be incorporated into physiological monitoring system 100 of FIG. 1 in which, for example, input signal generator 410 may be implemented as part of sensor 102, or into physiological monitoring system 310 of FIG. 3 in which, for example, input signal generator 410 may be implemented as part of sensor unit 312 of FIG. 3, and processor 412 may be implemented as part of monitor 104 of FIG. 1 or as part of monitor 314 of FIG. 3. Furthermore, all or part of system 400 may be embedded in a small, compact object carried with or attached to the subject (e.g., a watch, other piece of jewelry, or a smart phone). In some embodiments, a wireless transceiver (not shown) may also be included in system 400 to enable wireless communication with other components of physiological monitoring systems 100 of FIG. 1 and 310 of FIG. 3. As such, physiological monitoring systems 100 of FIG. 1 and 310 of FIG. 3 may be part of a fully portable and continuous subject monitoring solution. In some embodiments, a wireless transceiver (not shown) may also be included in system 400 to enable wireless communication with other components of physiological monitoring systems 100 of FIG. 1 and 310 of FIG. 3. For example, pre-processor 420 may output signal 416 over BLUETOOTH, 802.11, WiFi, WiMax, cable, satellite, Infrared, or any other suitable transmission scheme. In some embodiments, a wireless transmission scheme may be used between any communicating components of system 400. In some embodiments, system 400 may include one or more communicatively coupled modules configured to perform particular tasks. In some embodiments, system 400 may be included as a module communicatively coupled to one or more other modules.

It will be understood that the components of signal processing system 400 that are shown and described as separate components are shown and described as such for illustrative purposes only. In other embodiments the functionality of some of the components may be combined in a single component. For example, the functionality of processor 412 and pre-processor 420 may combined in a single processor system. Additionally, the functionality of some of the components shown and described herein may be divided over multiple components. Additionally, signal processing system 400 may perform the functionality of other components not show in FIG. 4. For example, some or all of the functionality of control circuitry 110 of FIG. 1 may be performed in signal processing system 400. In other embodiments, the functionality of one or more of the components may not be required. In an embodiment, all of the components can be realized in processor circuitry.

In some embodiments, any of the processing components and/or circuits, or portions thereof, of FIGS. 1, 3, and 4 may be referred to collectively as processing equipment. For example, processing equipment may be configured to amplify, filter, sample and digitize input signal 416 (e.g., using an analog-to-digital converter), and calculate physiological information from the digitized signal. Processing equipment may be configured to generate light drive signals, amplify, filter, sample and digitize detector signals, and calculate physiological information from the digitized signal. In some embodiments, all or some of the components of the processing equipment may be referred to as a processing module.

Figure 5:
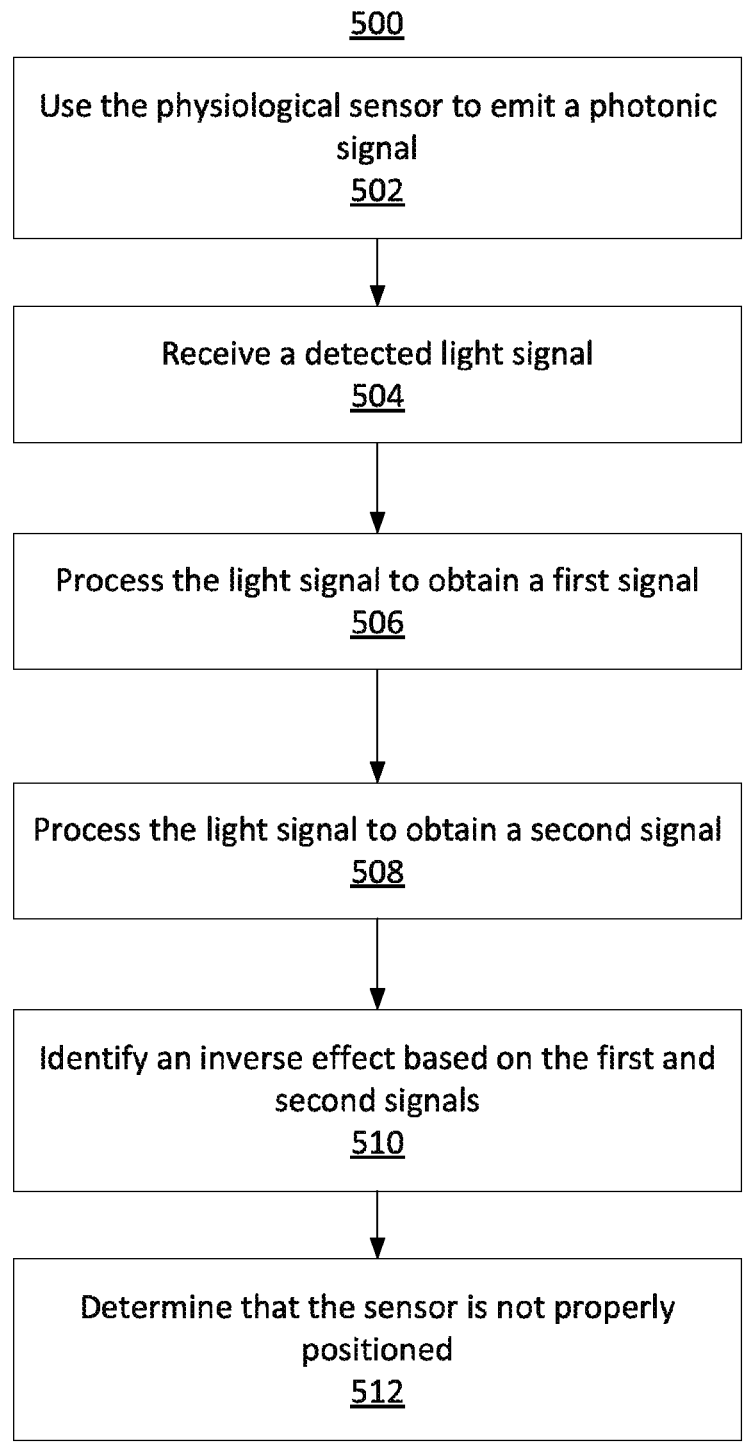
FIG. 5 is a flow diagram showing illustrative steps for determining a probe-off condition in accordance with some embodiments of the present disclosure.

FIG. 5 is flow diagram 500 showing illustrative steps for determining a probe-off condition in accordance with some embodiments of the present disclosure.

In step 502, the system may use the physiological sensor to emit a photonic signal. The system may emit a photonic signal including one wavelength of light, multiple wavelengths of light, a broad spectrum light (e.g., white light), any other suitable light, or any combination thereof. For example, the photonic signal may include light from a red LED and light from an IR LED. The emitted photonic signal may be emitted, for example, by light source 130 of FIG. 1. In some embodiments, the emitted photonic signal may include a light drive modulation, such as the light drive modulation of FIG. 2A. For example, where the photonic signal includes a red light source and an IR light source, the light drive modulation may include a red drive pulse followed by an "off" period followed by an IR drive pulse followed by an off period. It will be understood that this drive cycle modulation is merely exemplary and that any suitable drive cycle modulation or combination of modulations may be used. In some embodiments, the photonic signal may include a cardiac cycle modulation, where the brightness, duty cycle, firing rate, other parameters, or any combination thereof of one or more emitters and/or detectors are varied at a rate substantially related to the cardiac cycle.

In step 504, the system may receive a detected light signal. The received light signal may include the detected light signal and the detected ambient signal as described above. In some embodiments, the received light signal may in part correspond to the photonic signals of step 502, light from ambient sources, any other suitable source, or any combination thereof. The detected light signal may be detected by, for example, detector 140 of FIG. 1. In some embodiments, a portion of the emitted light may be partially attenuated by the tissue of the subject before being received as a received light signal. In some embodiments, the detected light signal may have been primarily reflected by the subject. For example, reflected light may be detected by a forehead-attached system where the emitter and detector are on the same side of the subject. In some embodiments, the received light may be have been transmitted through the subject. For example, transmitted light may be detected in a fingertip-attached or earlobe-attached sensor.

In some embodiments, the system may adjust or compensate a detected signal depending in part on the LED drive signal, the detector gain, other suitable system parameters, or any combination thereof. For example, increasing the gain on a detected signal may result in an increased ambient signal. The system may compensate for this increase in ambient light that is not correlated with a change in the sensor positioning. In a further example, the system may change the LED emitter brightness, resulting in a change in the detected signals. The system may compensate for these changes in the detected signal amplitude to distinguish them from a change in the sensor positioning. It will be understood that the system may make any adjustments in gain, amplification, frequency, wavelength, amplitude, any other suitable adjustments, or any combination thereof. It will be understood that the adjustments may be made to the emitted photonic signal, the received signal, a signal following a number of processing steps, any other suitable signals, or any combination thereof.

In step 506, the system may process the light signal to obtain a first signal. The first signal may correspond to an ambient signal. In some embodiments, the ambient signal may, for example, include ambient signal 222 of FIG. 2. In some embodiments, the ambient light drive signal may relate to "off" period 220 of FIG. 2. In some embodiments, the system may subtract an ambient signal such as ambient signal 222 of FIG. 2 from a received signal such as peak amplitude signal 224 of FIG. 2 to generate a signal such as pulsatile amplitude signal 226 of FIG. 2. In some embodiments, the signal with an ambient component subtracted and/or the received signal may be used to determine physiological parameters and identify a probe-off condition. In some embodiments, the system may determine an ambient signal for probe-off analysis before generating the pulsatile amplitude signal. Separation of the ambient signal from the received signal may include, for example, demultiplexer 156 of FIG. 1. Signal processing of the ambient component and emitted light component may include any suitable components of physiological monitoring system 100 of FIG. 1, physiological monitoring system 310 of FIG. 3, any other suitable components, or any combination thereof.

The first light signal may exhibit characteristics of the ambient signal. The system may determine one or more characteristics of the ambient signal including the signal level, amplitude, rate of change, slope, moving average, other trend, any other suitable characteristic, or any combination thereof. For example, a trend may include a first derivative of the amplitude signal. A characteristic may include a combination of parameters. For example, a trend may include the magnitude and polarity of the first derivative. In another example, the characteristic may include the signal amplitude and the polarity of the first derivative. Characteristics may be relative, absolute, or any combination thereof. For example, the signal level may be the absolute amplitude. In another example, the signal level may be relative to a baseline or to another signal. Determining the signal level may include any suitable processing equipment such as the processing equipment described above. The system may apply to the first signal any suitable filtering technique, smoothing technique, averaging technique, any other suitable technique, or any combination thereof. For example, the first signal may be filtered to remove noise. In another example, the signal may be smoothed or averaged to remove transient components.

In step 508, the system may process the light signal to obtain a second signal. The second signal may correspond to the emitted photonic signal and ambient light. In some embodiments, the second signal may relate to the signal received during a drive pulse, such as drive pulse 202 of FIG. 2. In some embodiments, the second signal may not include ambient light. The second signal may correspond to one or more wavelengths of emitted light. For example, the second signal may be an IR signal, a red signal, or a signal corresponding to any other suitable wavelength. In a further example, the second signal may correspond to multiple wavelengths combined by any suitable technique. The second signal may include one or more components of the light signal received in step 504. The system may determine characteristics and trends such as those described for the first signal in step 506. In some embodiments, the system may apply to the light signal any suitable filtering and processing as described for the first signal in step 504.

In some embodiments, the system may process a pulsatile amplitude signal based on the first signal and the second signal. This pulsatile amplitude signal may be referred to as the "DL−AM signal," or "DL minus AM" where "DL" refers to the detected light signal, AM refers to the detected ambient signal, and "DL−AM" refers to the subtraction of the second from the first. It will be understood that this signal name is merely exemplary and that the system may process any suitable signals based on the first signal, the second signal, and any other suitable information. For example, processed signals may include the result of subtracting the ambient from any photonic signal, the result of subtracting any first signal or combination of signals from any second signal or combination of signals, from any other suitable technique, or any combination thereof. In a further example, the DL−AM signal may include the result of subtracting the ambient signal from the IR photonic signal. In a further example, a Red-AM signal may be generated and used in place of the DL−AM signal by subtracting the ambient signal from a red signal. In a further example, a DL−AM signal may be generated and used in place of the DL−AM signal by subtracting the ambient signal from a combination of IR and Red signals. In some embodiments, the DL−AM signal may correspond to pulsatile amplitude signal 226 of FIG. 2. It will be understood that in some embodiments, the ambient signal will not be subtracted and the system may identify an inverse effect based in part on comparisons with the detected light signal.

In step 510, the system may identify an inverse effect based on the first and second signals. In some embodiments, the system may identify the presence of the inverse effect as being indicative of a probe-off condition. In some embodiments, an inverse effect may include opposite behavior in the ambient signal and the DL−AM signal. For example, the ambient signal and the DL−AM signal may vary in a substantially opposite manner. In a further example, the ambient signal may change in a substantially similar manner to the inverted DL−AM signal. In some embodiments, the system may identify the inverse effect using a metric, using a Lissajous technique, using a covariance, by any other suitable technique, or any combination thereof. For example, the system may use both a covariance and a metric to determine an inverse effect. In another example, the system may use only a metric.

The metric technique will be described in detail below in relation to FIG. 9. In the metric technique, the system may determine a weight indicative of the strength of the combined fluctuations in the first and second signals. The system may determine a count indicative of the number of times the first and second signals are of opposite polarity. The system may determine a metric based on the weight and the count, and use that metric to set a signal flag and/or determine an inverse effect.

A Lissajous technique may include comparing the alternating components of the first signal to the alternating components of the second signal. For example, the first signal may include an amplitude component varying with time (i.e., AC) and a constant component that is constant with time (i.e., DC). The second signal may also include an AC and a DC component. In some implementations, signals may be plotted against each other as a Lissajous figure. For example, the AC components of both signals may be identified and plotted against each other such that the alternating current amplitude of the first signal is plotted along a first axis and the alternating current amplitude of the second signal is plotted along a second axis. If the two signals vary in phase, that is to say, increase and decrease together in time, the Lissajous figure may appear as a scatter plot with points substantially resembling a linear curve with positive slope. If the two signals are of opposite polarity (i.e., 180 degrees out of phase) the Lissajous figure may include a scatter plot with points substantially resembling a linear curve with negative slope. In some embodiments, a Lissajous figure resembling a line of negative slope may be recognized as being indicative of an inverse effect. In some embodiments, processing of the Lissajous figure may include curve fitting, linear regression, least squares regression, least median squares regression, Monte Carlo processing, multi-parameter curve fitting, other suitable regression techniques, or any combination thereof. Other shapes, such as circles and ellipses, may be indicative of phase shifts intermediate to 0 and 180 degrees. The system may recognize outliers, noise, and other elements of the Lissajous figure as being indicative of an inverse effect. It will be understood that the plotting technique described herein is merely exemplary and that any suitable implementation of a Lissajous technique may be used. For example, the system may process the signals using a Lissajous technique without generating a Lissajous figure.

A covariance technique may be used to identify an inverse effect. Covariance is a statistical quantification of how much two variables change together. For example, the covariance of the first and second signals may be calculated to determine if they are changing together in time. In some embodiments, strongly correlated signals may have a positive covariance, uncorrelated signals may have a covariance of zero, and inversely correlated signals may have a negative covariance. The system may recognize a negative covariance between the detected ambient signal and the DL−AM signal as being indicative of an inverse effect. The system may also recognize a positive covariance between the detected ambient signal and the inverted DL−AM as being indicative of an inverse effect. In some embodiments, the covariance may be considered over a time window or a moving average. In some embodiments, the covariance may be compared to a threshold or target value. It will be understood that the use of covariance described herein is merely exemplary and that the system may use any suitable application of covariance to any suitable signal or combination of signals. It will also be understood that any suitable statistical functions may be used in place of, in addition to, or in combination with covariance.

In step 512, the system may determine that the physiological sensor is not properly positioned. The system may determine this based on the identification of an inverse effect. For example, if the system identifies an inverse effect, it may identify a probe-off condition. In some embodiments, the identification of an inverse effect may be used in combination or in addition to other suitable indicia of a probe-off condition. For example, the system may identify ambient signal levels, mimicking or following of two or more signals, signal flatness, any other suitable condition, or any combination thereof. In some embodiments, the system may use multiple criteria to determine a probe-off condition. The multiple indicators may be combined using any suitable logic technique, algorithmic technique, polling technique, weighting technique, any other suitable technique, or any combination thereof. In some embodiments, the sequence of indicators may be included in determining a probe-off condition. In some embodiments, the system may determine a confidence value related to the possibility of a probe-off condition based on a plurality of criteria.

The following FIGS. 6, 7, 8, and 10 show illustrative signals used in determining a probe off condition, for example, by a pulse oximeter. It will be understood that the signals of FIGS. 6, 7, 8, and 10 may be filtered, processed, scaled, or otherwise modified such that typical pulse features are not illustrated. For example, the periodic plethysmography waveforms may not be visible due to the horizontal and or vertical scale of the plots. In another example, the signals may be filtered by the system to remove these variations for the purposes of determining a probe-off condition. It will be understood that these signals and plots are merely exemplary and that any suitable signals and analysis may be used. It will also be understood that while the particular features of these signals may be unique to an optical pulse oximeter, the technique described herein may be applied to other systems. It will also be understood that the particular signals displayed in FIGS. 6, 7, 8, and 10 may or may not be determined by the system, may or may not be plotted, and may or may not be displayed to the user, as suitable based on the particular arrangement. For example, some of the signals are illustrated herein as examples of an inverse effect occurring, though the system may not use those particular signals to identify the inverse effect.

Figure 6:
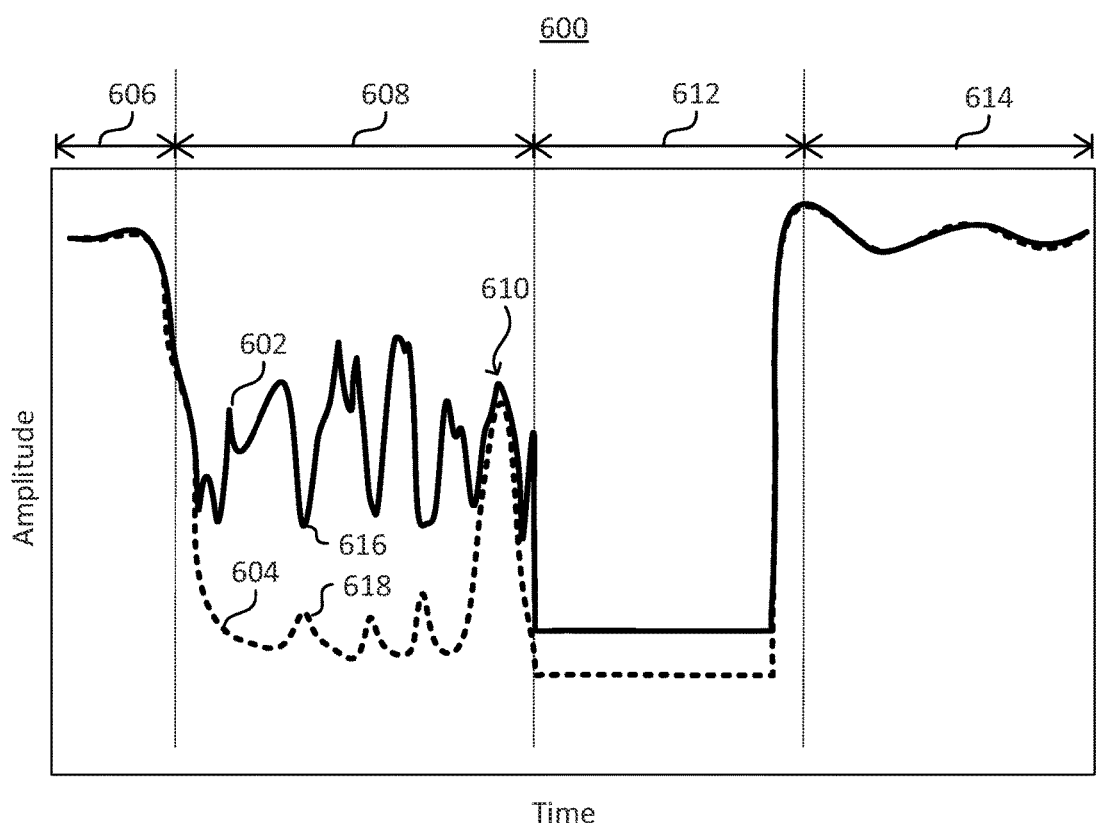
FIG. 6 shows an illustrative plot of system signals in accordance with some embodiments of the present disclosure.

FIG. 6 shows illustrative plot 600 of system signals in accordance with some embodiments of the present disclosure. Plot 600 may show units of time on the abscissa axis. For example, plot 600 may show approximately 40 seconds of received signals. It will be understood that the boundaries of indicated time intervals are merely illustrative. Plot 600 may show units of amplitude on the ordinate axis. Plot 600 may include detected light signal 602 and detected ambient signal 604. Detected ambient signal 604 may correspond to the first signal processed in step 506 of FIG. 5. Detected signal 602 may correspond to the second signal processed in step 508 of FIG. 5. It will be understood that detected light signal 602 may correspond to any suitable wavelength or combination of wavelengths, such as red and IR light. It will also be understood that detected light signal 602 may include both information from both ambient light and an emitted photonic signal.

The signals of plot 600 may correspond to signals received by an optical pulse oximeter sensor moving relative to a reflective surface. For example, the sensor may be moving in a range between approximately 2 mm and 20 mm from a reflective surface.

In time intervals 606 and 614, the detector may be detached from a patient and far from any reflective surface. This may result in the following or mimicking behavior illustrated in those time intervals, where the majority of the light contributing to detected light signal 602 and detected ambient signal 604 is ambient, and thus the same or similar amount of light contributes to both signals.

In time interval 608, the detector may be moving close to a reflective surface. This may result in detected light signal 602 changing inversely with respect to detected ambient signal 604. For example, trough 616 of detected light signal 602 may be substantially aligned with peak 618 of detected ambient signal 604. As described above, this behavior may be caused due to increased shading of ambient light and increased reflection of the photonic signal. At peak 610, the amount of reflected light reaching the detector may be briefly reduced, resulting in detected light signal 602 following detected ambient signal 604. In some embodiments, the behavior at peak 610 may be similar to behavior in time interval 614. In some embodiments, the behavior in time interval 608 may be identified by the system as being indicative of an inverse effect.

In time interval 612, the sensor may be positioned at a fixed distance from a surface. This results in the substantially constant amplitudes in those time intervals. In some embodiments, the sensor may be near a reflective surface, resulting in some reflected light reaching the detector.

Figure 7:
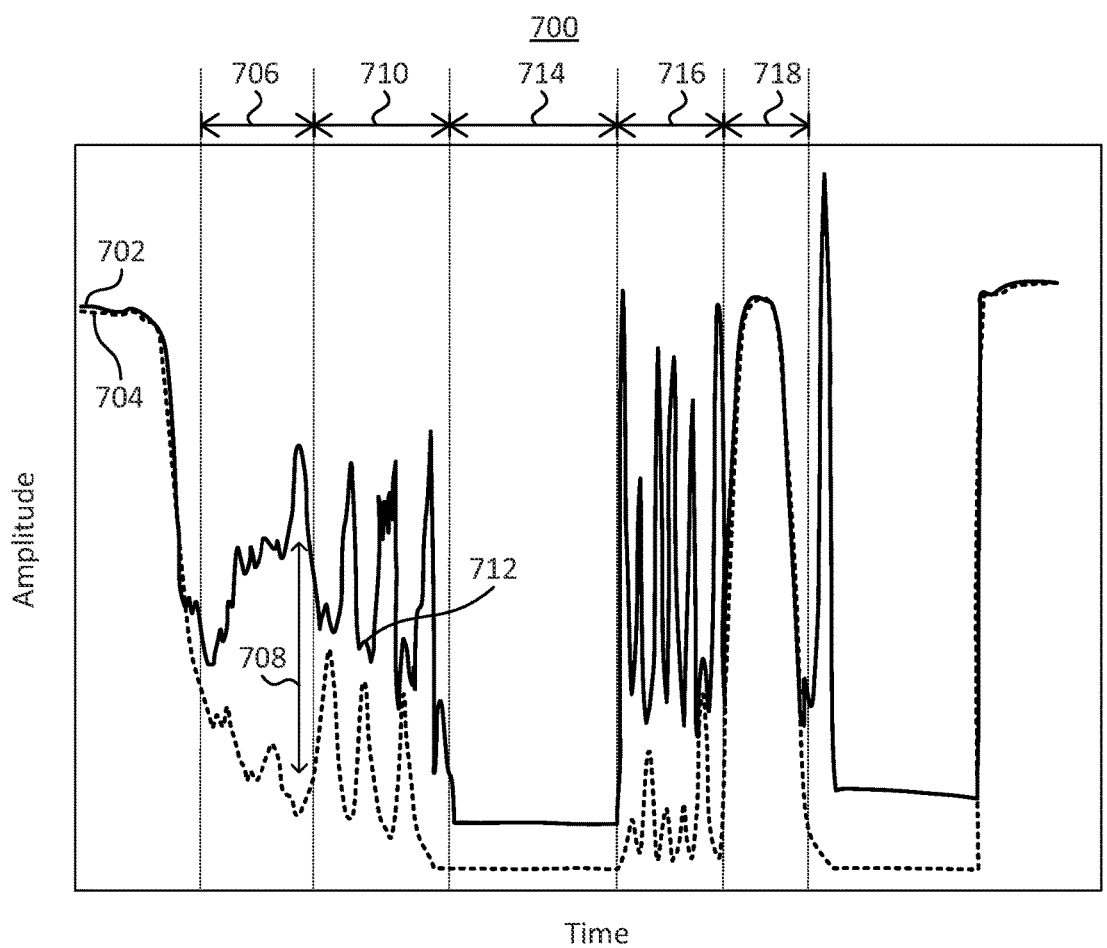
FIG. 7 shows another illustrative plot of system signals in accordance with some embodiments of the present disclosure.

FIG. 7 shows illustrative plot 700 of system signals in accordance with some embodiments of the present disclosure. Plot 700 may show units of time on the abscissa axis. For example, plot 700 may show approximately 35 seconds of received signals. It will be understood that the boundaries of illustrated time intervals are merely exemplary. Plot 700 may show units of amplitude on the ordinate axis. Plot 700 may include detected light signal 702 and detected ambient signal 704. Detected ambient signal 704 may correspond to the first signal processed in step 506 of FIG. 5. Detected light signal 702 may correspond to the second signal processed in step 508 of FIG. 5. It will be understood that detected light signal 702 may correspond to any suitable wavelength or combination of wavelengths. It will also be understood that detected light signal 702 may include both information from both ambient light and an emitted photonic signal. The signals of plot 700 may correspond to signals received by an optical pulse oximeter sensor moving relative to a reflective surface.

In time interval 706, the sensor may be moving relative to a reflective surface at a close distance. In time interval 710, the sensor may be moving relative to a reflective distance at a far distance. For example, "close" may correspond to approximately 5 mm and far may correspond to approximately 50 mm. In time interval 706, the system may identify an inversion effect. For example, at point 708, a peak may be observed in detected light signal 702 concurrent with a trough in detected ambient signal 704. In time interval 710, changes in detected ambient signal 704 may make an increasingly substantial contribution to the amplitudes of detected light signal 702, where detected light signal 702 includes information from both ambient light and photonic signals, such as that received in detector current waveform 214 of FIG. 2. This behavior may be observed in the small local peaks in the troughs of detected light signal 702 such as peak 712.

In time interval 714, the sensor may be positioned at a fixed distance from a reflective surface, and thus no variations in the signal amplitudes may be observed.

In time interval 716, the sensor may be moving at a distance from a reflective surface closer than the distance in time interval 710, and thus the signals may be observed to vary inversely. For example, a peak in detected light signal 702 may be concurrent with a valley in detected ambient signal 704. In time interval 716, a portion of light reflected from the emitters may reach the detector, and some shading of the ambient light may occur, resulting in the signal patterns illustrated in time interval 716. In some embodiments, the negative correlation behavior between detected light signal 702 and ambient signal 704 in time interval 716 may be determined to be an inverse effect. In some embodiments, the system may identify a probe-off condition in time interval 716 based on the identification of the inverse effect. In some embodiments, the inverse effect relating to this behavior may be more apparent as plotted in region 810 of FIG. 8, as described below.

In time interval 718, the sensor may be moved very far from any surface, such that the amount of light from the emitters that reaches the detectors is effectively zero. In some embodiments, detected light signal 702 and detected ambient signal 704 may correspond to ambient light, and thus may follow or mimic each other.

Figure 8:
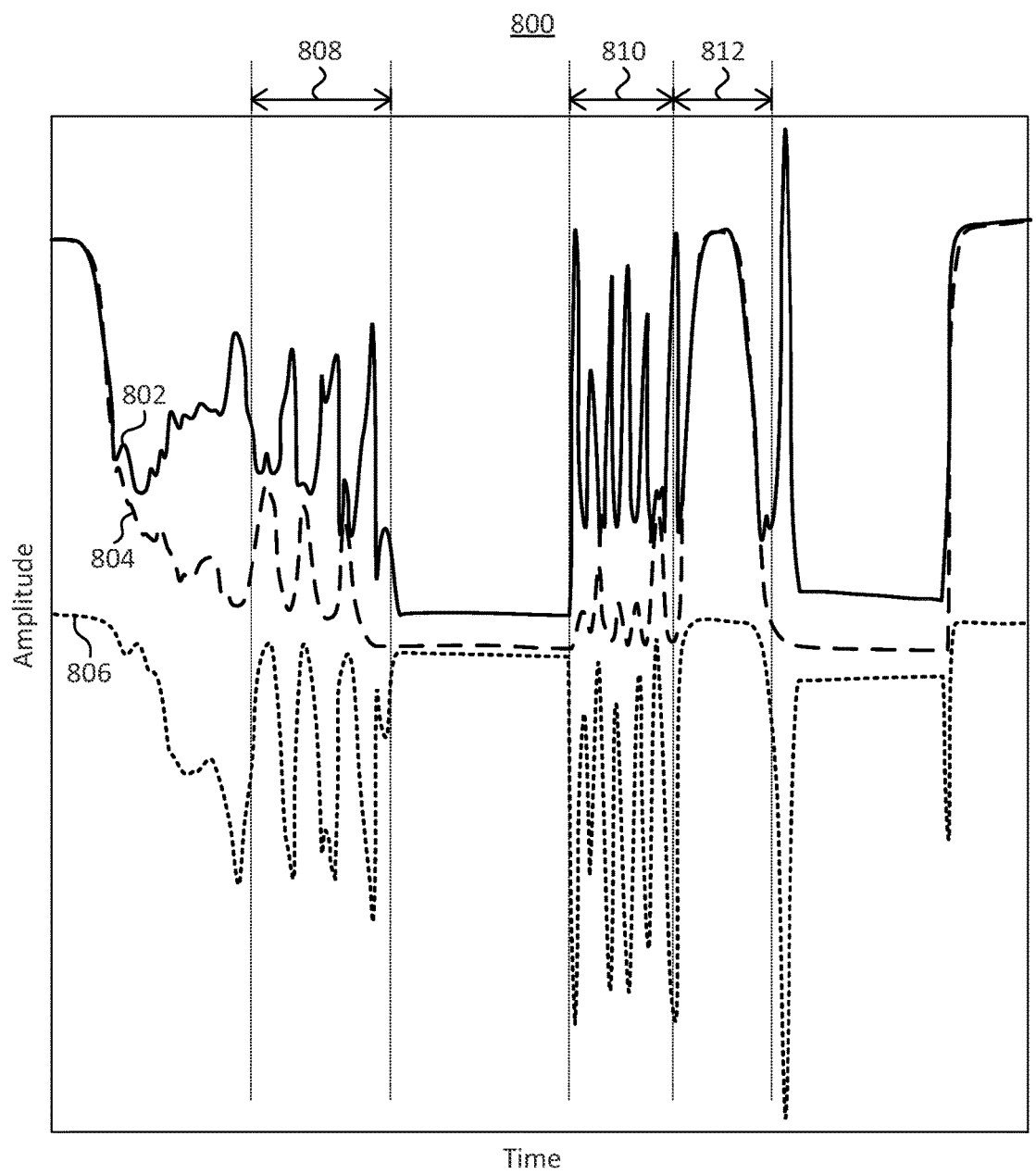
FIG. 8 shows another illustrative plot of system signals in accordance with some embodiments of the present disclosure.

FIG. 8 shows illustrative plot 800 of system signals in accordance with some embodiments of the present disclosure. Plot 800 may show units of time on the abscissa axis. For example, plot 800 may show approximately 35 seconds of received signals. It will be understood that the boundaries of illustrated time intervals are merely exemplary. Plot 800 may show units of amplitude on the ordinate axis. The signals of plot 800 may correspond to signals received by an optical pulse oximeter sensor moving relative to a reflective surface. Plot 800 may include detected light signal 802, detected ambient signal 804, and inverted difference signal 806. The inverted difference signal is used here for purposes of illustration so that the difference signal does not overlap with detected ambient signal 804. It will be understood that while the inverted difference signal can be used to identify an inverse effect, it is not needed to identify such an effect. For example, similar behavior of the ambient and the inverted DL−AM ambient signal may correspond to opposite behavior in the ambient and the difference signal. Detected ambient signal 804 may correspond to the first signal processed in step 506 of FIG. 5. Detected light signal 802 may correspond to the second signal processed in step 508 of FIG. 5. It will be understood that detected light signal 802 may correspond to any suitable wavelength or combination of wavelengths. It will also be understood that detected light signal 802 may include both information from both ambient light and an emitted photonic signal. Inverted difference signal 806 may correspond to the inverted result of subtracting detected ambient signal 804 from detected light signal 802. For example, inverted difference signal 806 may be referred to as an "−(DL−AM)" signal. Inverted difference signal 806 may correspond to the inverse of the pulsatile amplitude signal 226 of FIG. 2 after demultiplexing. In some embodiments, the system may identify correlated behavior in detected ambient signal 804 and inverted DL−AM signal 806, which may be determined to be indicative of an inverse effect. For example, an inverse effect may be observed by determining correlated behavior in detected ambient signal 804 and inverted difference signal 806 in time interval 808 and time interval 810.

Figure 9:
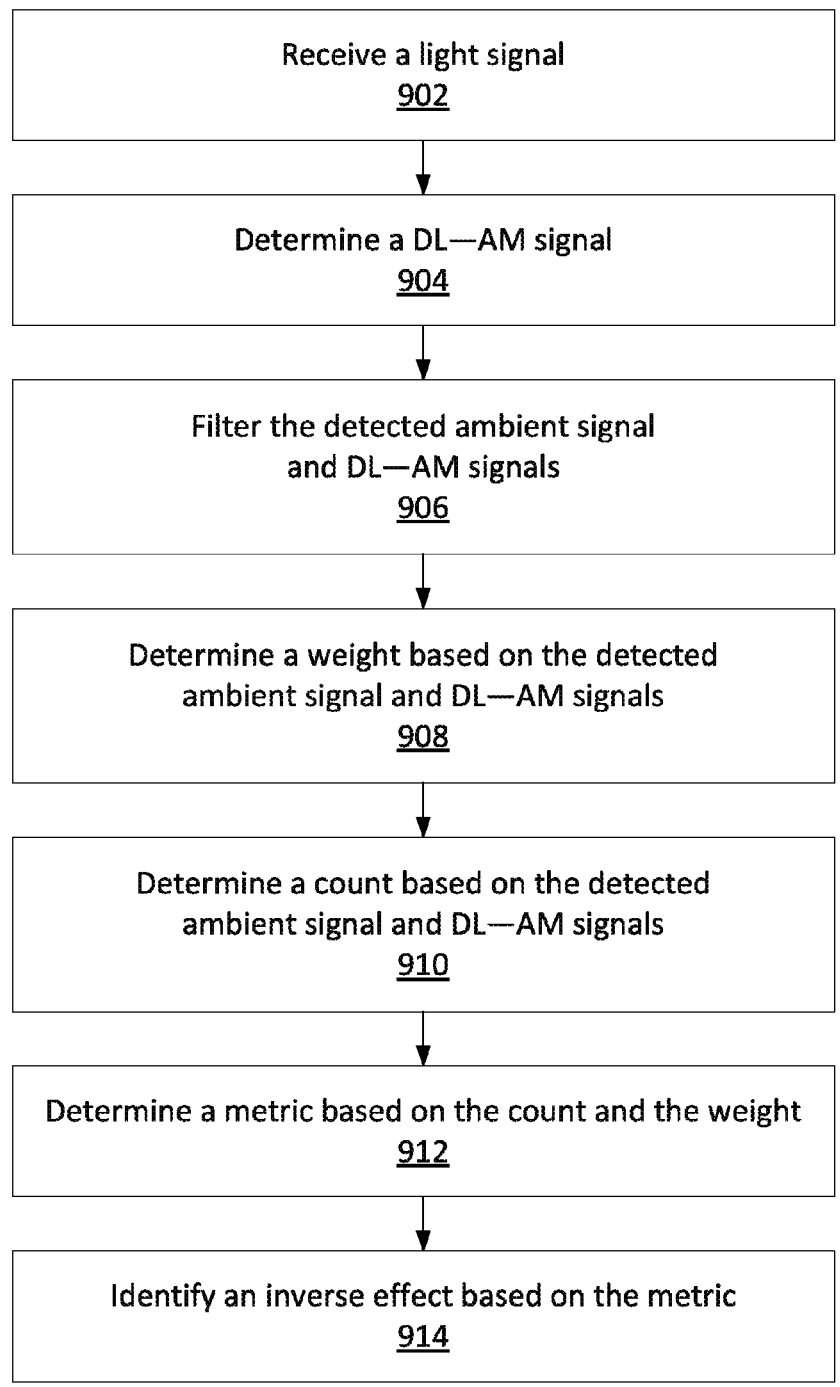
FIG. 9 is a flow diagram showing illustrative steps for determining an inverse effect using a metric in accordance with some embodiments of the present disclosure.

FIG. 9 is flow diagram 900 showing illustrative steps for determining an inverse effect using a metric in accordance with some embodiments of the present disclosure.

In step 902, the system may receive a light signal. In some embodiments, the received light signal may in part correspond to the photonic signals from an emitter, light from ambient sources, any other suitable source, or any combination thereof. The received light signal may include the detected light signal and the detected ambient signal as described above in step 502 of FIG. 5. The ambient signal may correspond to, for example, the first light signal processed in step 506 of FIG. 5. The detected light signal may correspond to, for example, the second light signal processed in step 508 of FIG. 5. In some embodiments, the detected light signal may include information related to an emitted photonic signal and ambient light.

In step 904, the system may determine an DL−AM (i.e., detected light minus ambient) signal. The DL−AM signal may be determined by subtracting an ambient light signal from the detected light signal of step 902. The ambient signal may include light received by a detector that is not related to a particular emitted photonic signal. The ambient signal may correspond to, for example, the first light signal processed in step 506 of FIG. 5. In some embodiments, the ambient signal may relate to light received during "off" pulses 220 of FIG. 2. In some embodiments, the ambient signal may relate to ambient signal 222 of FIG. 2. The DL−AM signal may be calculated using Eq. 2:

$$(DL-AM)=(DL)-(AM) \qquad (2)$$

where DL is detected light signal of step 902 and AM is the detected ambient signal of step 902.

In step 906, the system may filter the detected ambient signal and the result of subtracting the detected ambient signal from the detected light signal (DL−AM). In some embodiments, the signals may be filtered within a range of expected cardiac pulses. For example, signals may be filtered with a bandpass filter from 0.5 Hz to 4 Hz (i.e., 30 to 240 beats per minute). In some embodiments, this filtering may remove noise, motion, other non-cardiac pulsatile signals, or any combination thereof. It will be understood that the filtering technique described herein is merely exemplary and that the system may use any suitable hardware filters, software filters, any other suitable processing steps, or any combination thereof. For example, the system may use high pass filters, low pass filters, bandpass filters, or band notch filters. Any suitable implementation of these filters such as RC, LC, RLC, Bessel filters, Butterworth filters, Chebyshev filters, Elliptic filters, biquadratic filters, Op-Amp filters, active filters, passive filters, any other suitable filters, any software implementation of filters, or any combination thereof.

In step 908, the system may determine a weight based in part on the ambient light signal and the DL−AM signal. In some embodiments, the weight may be determined using filtered signals. In some embodiments, the system may determine a weight by dividing the summation of the product of the instantaneous absolute values across a time delay divided by the number of samples in the summation, and then taking the square root of the quotient. The time delay may be, for example, 4 seconds. In some embodiments, the system may determine a weight using Eq. 3:

$$W = \sqrt{\frac{\sum_{i=1}^{N}(|(AM)_i|\cdot|(DL-AM)_i|)}{N}} \qquad (3)$$

where W is the weight, AM and DL−AM are defined as above, and N is the number of samples. It will be understood that in some embodiments, the system may use a filtered, normalized, averaged, or otherwise suitably modified version of the signals. For example, filtering of the signals is shown in plot 1020 of FIG. 10 discussed below. It will be understood that this is a discrete formula which may in some embodiments be preferable for discrete data. In some embodiments, Eq. 2 may be replaced with a continuous function. For example, Eq. 2 may include an integral in place of a summation, where the ambient light signal and DL-AM signal are continuous signals. It will be understood that the aforementioned technique for determining a weight is merely exemplary and that any suitable technique for determining a weight indicative of the signal fluctuations may be used. It will also be understood that any suitable signals may be used in determining a weight. For example, the detected light signal and the DL-AM signal may be used with a related equation.

In step 910, the system may determine a count based on the ambient light signal and the DL-AM signal. The count may include a count of the number of times that the detected ambient signal and the DL-AM signals are of opposite polarity. The count may correspond to a digital value of the occurrence of an inverse effect. In some embodiments, the system may use the filtered detected ambient signal and DL-AM signal to determine a count. The count may be performed over any suitable time window. For example, the count may be determined for each value of a discrete signal. For example, if the detected ambient signal and the DL-AM signal are of opposite polarity for a given sample or value of a discrete signal, the count may be increased by one. If the detected ambient signals and DL-AM signals are of the same polarity, the count may be decreased by one. It will be understood that this technique of determining a count is merely exemplary and that any suitable technique may be used.

In some embodiments, the system may determine a scaled count. The scaled count may include information from the count. In some embodiments, the scaled count may be set to zero when the count crosses a threshold. The scaled count may be scaled to fit within a range. For example, the values of the count may be scaled to a range between 0 and 1 when the count is above a threshold, and set to 0 when below a threshold.

In step 912, the system may determine a metric based on the count and the weight. The system may determine a metric by multiplying the weight determined in step 908 by the scaled count determined in step 910. The product of this multiplication may be the metric. It will be understood that this determination of a metric is merely exemplary and that any suitable technique to determine a metric may be used. For example, determining the metric may include any suitable signals or combination of signals. Determining the metric may include normalization, scaling, interpolation, decimation, regression, curve fitting, refinement, any other suitable processing, or any combination thereof.

In step 914, the system may identify an inverse effect based on the metric. In some embodiments, the system may compare the metric to a threshold or target parameter. For example, if the metric is above a predetermined value, the system may set a flag, trigger an alarm, generate an output, generate any other suitable output, or any combination thereof. In some embodiments, the threshold may be determined based on predetermined values, based on user input, based on clinical parameters, based on system parameters, based on the sensor or probe type, based on historical information, based on any other suitable parameters, or any combination thereof. In some embodiments, the system may compare the metric to a constant threshold, to a moving threshold, to any other suitable threshold, or any combination thereof. In some embodiments, the system may compare a characteristic of the metric to a threshold or target parameter. For example, the system may use a derivative, moving average, smoothed value, integral, any other suitable characteristic, or any combination thereof to determine an inverse effect.

Figure 10:
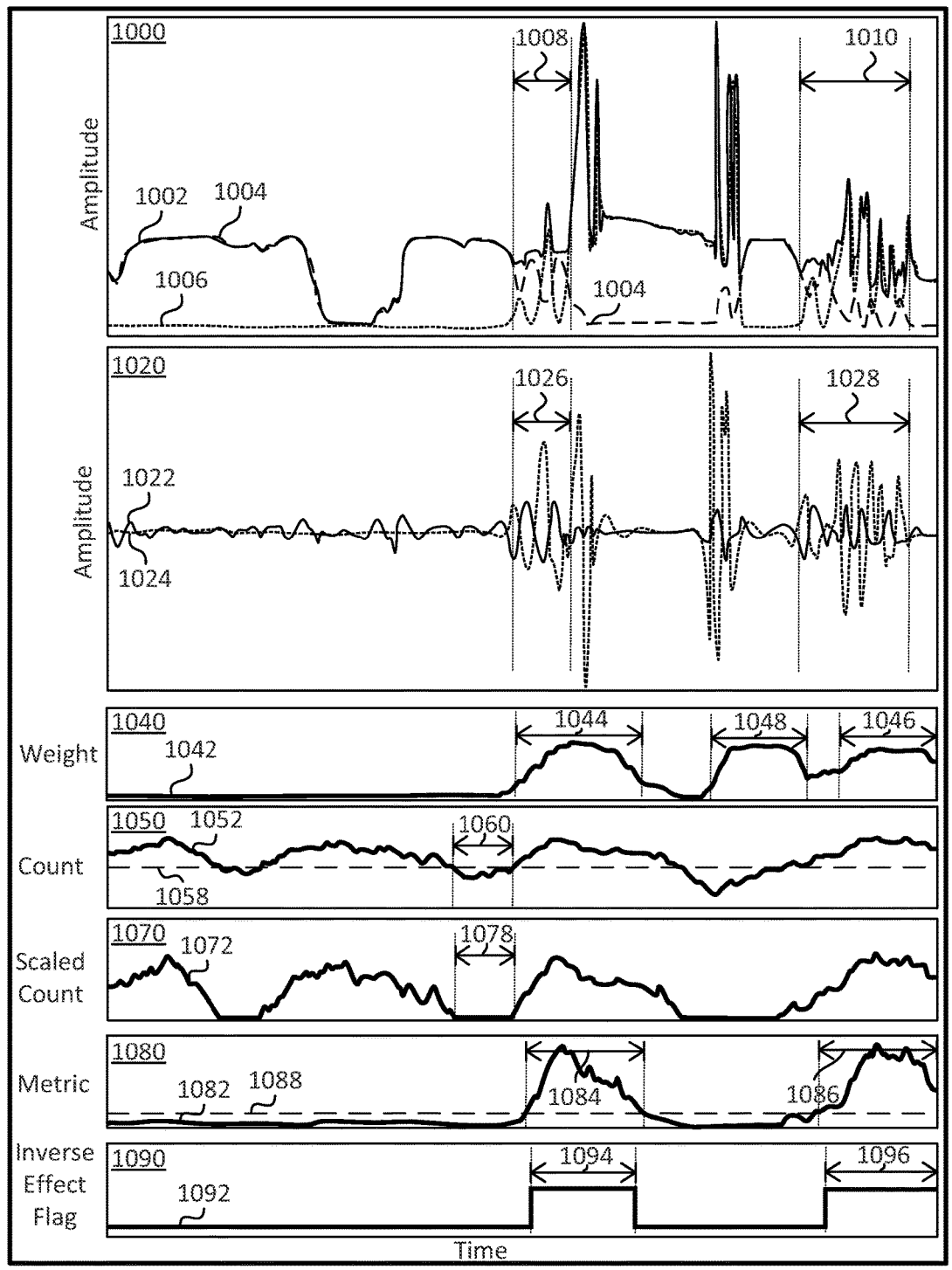
FIG. 10 is a panel showing illustrative plots of system signals including using a metric to determine an inverse effect in accordance with some embodiments of the present disclosure.

FIG. 10 is a panel showing illustrative plots of system signals including using a metric to determine an inverse effect in accordance with some embodiments of the present disclosure. FIG. 10 includes signal plot 1000, filtered signal plot 1020, weight plot 1040, count plot 1050, scaled count plot 1070, metric plot 1080, and inverse effect flag plot 1090. The abscissa of all the plots of FIG. 10 may be on a common time scale.

Signal plot 1000 may include received signals from, for example, a detached forehead pulse oximeter sensor. Signal plot 1000 may show units of time on the abscissa axis. For example, signal plot 1000 may show approximately 50 seconds of received signals. It will be understood that the boundaries of illustrated time intervals are merely exemplary. Signal plot 1000 may show units of amplitude on the ordinate axis. The signals of signal plot 1000 may correspond to signals received by an optical pulse oximeter sensor moving relative to a reflective surface. Signal plot 1000 may include detected light signal 1002, detected ambient signal 1004, and DL-AM signal 1006. Detected ambient signal 1004 may correspond to the first signal processed in step 506 of FIG. 5. Detected light signal 1002 may correspond to the second signal processed in step 508 of FIG. 5. Detected light signal 1002 may include information related to the received light signal determined in step 902 of FIG. 9. It will be understood that detected light signal 1002 may correspond to any suitable wavelength or combination of wavelengths. It will also be understood that detected light signal 1002 may include information from both ambient light and an emitted photonic signal. DL-AM signal 1006 may be the result of subtracting detected ambient signal 1004 from detected light signal 1002. DL-AM signal 1006 may include information related to the DL-AM signal determined in step 904 of FIG. 9. As illustrated, an inverse effect can be seen in time interval 1008 and 1010 of signal plot 1000, although further processing may be desired to automatically identify and/or quantify the inverse effect, as will be detailed below.

Filtered signal plot 1020 may include the result of filtering signals from signal plot 1000. Filtered signal plot 1020 may include information related to the filtered signals determined in step 906 of FIG. 9. Filtered signal plot 1020 may show units of time on the abscissa axis. For example, filtered signal plot 1020 may show approximately 50 seconds of received signals. Filtered signal plot 1020 may show units of amplitude on the ordinate axis. The signals of filtered signal plot 1020 may correspond to filtered signals received by an optical pulse oximeter sensor moving relative to a reflective surface. Filtered signal plot 1020 may include filtered detected ambient signal 1022 and filtered DL-AM signal 1024. For example, the filtered signals may have been generated by applying a 0.5 Hz to 4 Hz software implemented bandpass filter to the detected ambient signal 1004 and DL-AM signal 1006. As illustrated, an inverse effect may be identified in time interval 1026 and time interval 1028.

Weight plot 1040 may include a weight calculated using Eq. 3 as described in step 908 of FIG. 9. Weight plot 1040 may show units of time on the abscissa axis. For example, weight plot 1040 may show approximately 50 seconds of received signals. Weight plot 1040 may show arbitrary units on the ordinate axis. Weight plot 1040 may include weight signal 1042. The weight signal may be indicative of the time intervals displaying fluctuations in the filtered signals of filtered signal plot 1020. In some embodiments, time interval 1044 and time interval 1046 may correspond to an inverse effect. In some embodiments, time interval 1048 may not correspond to an inverse effect, despite the relatively high level of the weight in that time interval.

Count plot 1050 may include a count calculated as described in step 910 of FIG. 9. Count plot 1050 may show units of time on the abscissa axis. For example, count plot 1050 may show approximately 50 seconds of received signals. Count plot 1050 may show arbitrary units on the ordinate axis. Count plot 1050 may include count signal 1052. Count signal 1052 may be indicative of the number of times that the filtered signals of filtered signal plot 1020 are of opposite polarity. Count plot may include threshold 1058, which may be used in determining the signals displayed in scaled plot 1070. As illustrated, count signal 1052 crosses below threshold 1058 in time interval 1060.

Scaled count plot 1070 may include a scaled count calculated as described in step 910 of FIG. 9. Scaled count plot 1070 may show units of time on the abscissa axis. For example, scaled count plot 1070 may show approximately 50 seconds of received signals. Scaled count plot 1070 may show arbitrary units on the ordinate axis of a specific range. For example, scaled count plot may range from 0 to 1 on the ordinate axis. Scaled count plot 1070 may include scaled count signal 1072. In some embodiments, scaled count signal 1072 may be set to zero when count 1052 is below threshold 1058. For example, time interval 1060 of count plot 1050 may correspond to time interval 1078 where scaled count signal 1052 is zero. It will be understood that any suitable scaling may be used to generate scaled count signal 1072. For example, scaling may include linear scaling, non-linear scaling, logarithmic scaling, any other suitable scaling, or any combination thereof. It will also be understood that the system may apply any suitable thresholds, zeroing, other processing techniques, or any combination thereof.

Metric plot 1080 may include a metric determined as described in step 912 of FIG. 9. Metric plot 1080 may show units of time on the abscissa axis. For example, metric plot 1080 may show approximately 50 seconds of received signals. Metric plot 1080 may show arbitrary units on the ordinate axis. Metric plot 1080 may include metric signal 1082. Metric signal 1082 may be generated by multiplying weight signal 1042 of plot 1040 by scaled count signal 1072 of plot 1070. It may be observed that the metric is at a relatively high signal level in time interval 1084 and time interval 1082, substantially correlated with time interval 1008 and time interval 1010 where an inverse effect was displayed in signal plot 1000. It may also be observed that the time interval corresponding in time to time interval 1048 of weight plot 1048 is at a low level due to the low level of the scaled count in that time interval. Similarly, time intervals of the scaled count with relatively high signal levels that correspond to a low level of the weight result in a low metric. Thus, in some embodiments, the metric may require a relatively high level of both the scaled count and the weight to generate a relatively high metric signal. Metric plot may include threshold 1088, which may be used in determining the signals displayed in inverse effect flag plot 1090.

Inverse effect flag plot 1090 may include information related to determining an inverse effect based on the metric as described in step 914 of FIG. 9. Inverse effect flag plot 1090 may show units of time on the abscissa axis. For example, inverse effect flag plot 1090 may show approximately 50 seconds of received signals. Inverse effect flag plot 1090 may show arbitrary units on the ordinate axis. Inverse effect flag plot 1090 may include inverse effect flag signal 1092. In some embodiments, inverse effect flag signal 1092 may be set to 0 (or a low value) when metric signal 1082 is below threshold 1088, and may be set to 1 (or a high value) when metric signal 1082 is above threshold 1088. For example, time intervals 1084 and 1086 of metric plot 1080 may correspond to high flag time intervals 1094 and 1096 of inverse effect flag plot 1090. In some embodiments, inverse effect flag signal 1092 may have a more complex relationship to metric signal 1082. For example, the flag may only be set if the metric exceeds a threshold for a certain amount of time, by a certain magnitude, by a product of the time and the magnitude, by any other suitable parameter, or any combination thereof. In some embodiments, the flag may only be set to 0 following being set to 1 after a certain amount of time has elapsed, by an external trigger, by a second threshold, by any other suitable parameter, or any combination thereof.

In some embodiments, the system may recognize the inverse effect flag as being indicative of a probe-off condition. In some embodiments, the system may use the inverse effect flag as part of a more complex algorithm for determining probe off conditions.

The foregoing is merely illustrative of the principles of this disclosure and various modifications may be made by those skilled in the art without departing from the scope of this disclosure. The above described embodiments are presented for purposes of illustration and not of limitation. The present disclosure also can take many forms other than those explicitly described herein. Accordingly, it is emphasized that this disclosure is not limited to the explicitly disclosed methods, systems, and apparatuses, but is intended to include variations to and modifications thereof, which are within the spirit of the following claims.

What is claimed:

1. A method for determining whether a pulse oximetry sensor is properly positioned on a subject, the method comprising:

receiving a detected light signal using the pulse oximetry sensor;

processing, using a pulse oximeter, the light signal to obtain a first signal corresponding to ambient light;

processing, using the pulse oximeter, the light signal to obtain a second signal corresponding to an emitted photonic signal and ambient light;

identifying, using the pulse oximeter, an inverse effect based on the first signal and the second signal, wherein the inverse effect corresponds to when two signals change inversely with respect to each other, wherein identifying the inverse effect comprises:

determining a difference signal by subtracting the first signal from the second signal;

determining a weight based on the first signal and the difference signal;

determining a count based on the first signal and the difference signal;

determining a metric based on the weight and the count; and comparing the metric to a threshold; and determining, using the pulse oximeter, that the pulse oximetry sensor is not properly positioned based on the identification of an inverse effect.

2. The method of claim 1, wherein determining the weight comprises:
- determining the product of multiplying the absolute value of the first signal by the absolute value of the difference signal for a given sample;
- determining a summation of the products for N number of samples; and
- determining a quotient by dividing the summation by N number of samples.

3. The method of claim 1, wherein determining the count comprises:
- identifying when the first signal and the difference signal change inversely with respect to each other; and
- incrementing the count based on when the first signal and the difference signal are identified as changing inversely with respect to each other.

4. The method of claim 1, wherein determining the metric based on the weight and the count comprises determining the product of multiplying the weight by the count.

5. The method of claim 1, wherein determining the inverse effect comprises using a technique selected from the group comprising Lissajous, covariance, or any combination thereof.

6. The method of claim 1, further comprising providing an indicator that the pulse oximetry sensor is not properly positioned.

7. A system for determining whether a pulse oximetry sensor is properly positioned on a subject, the system comprising:
- a pulse oximeter configured to:
  - receive a detected light signal using the pulse oximetry sensor;
  - process the light signal to obtain a first signal corresponding to ambient light;
  - process the light signal to obtain a second signal corresponding to an emitted photonic signal and ambient light;
  - determine a difference signal by subtracting the first signal from the second signal;
  - determine a weight based on the first signal and the difference signal;
  - determine a count based on the first signal and the difference signal;
  - determine a metric based on the weight and the count;
  - compare the metric to a threshold;
  - identify an inverse effect based on the first signal and the second signal, wherein the inverse effect corresponds to when two signals change inversely with respect to each other; and
  - determine that the pulse oximetry sensor is not properly positioned based on the identification of an inverse effect.

8. The system of claim 7, wherein the pulse oximeter is configured to determine the weight by:
- determining the product of multiplying the absolute value of the first signal by the absolute value of the difference signal for a given sample;
- determining a summation of the products for N number of samples; and
- determining a quotient by dividing the summation by N number of samples.

9. The system of claim 7, wherein the pulse oximeter is configured to determine the count by:
- identifying when the first signal and the difference signal change inversely with respect to each other; and
- incrementing the count based on when the first signal and the difference signal are identified as changing inversely with respect to each other.

10. The system of claim 7, wherein the pulse oximeter is configured to determine the metric by determining the product of multiplying the weight by the count.

11. The system of claim 7, wherein the pulse oximeter is configured to determine the inverse effect by using a technique selected from the group comprising Lissajous, covariance, or any combination thereof.

12. The system of claim 7, wherein the pulse oximeter is further configured to provide an indicator that the pulse oximetry sensor is not properly positioned.

* * * * *